(12) United States Patent
Hayashi et al.

(10) Patent No.: US 10,676,626 B2
(45) Date of Patent: Jun. 9, 2020

(54) INK JET TEXTILE PRINTING INK COMPOSITION AND INK RECEIVING CONTAINER

(71) Applicant: Seiko Epson Corporation, Tokyo (JP)

(72) Inventors: Hiroko Hayashi, Shiojiri (JP); Tetsuya Aoyama, Shiojiri (JP); Makoto Nagase, Shiojiri (JP)

(73) Assignee: Seiko Epson Corporation (JP)

( * ) Notice: Subject to any disclaimer, the term of this patent is extended or adjusted under 35 U.S.C. 154(b) by 294 days.

(21) Appl. No.: 15/715,756

(22) Filed: Sep. 26, 2017

(65) Prior Publication Data

US 2018/0086929 A1   Mar. 29, 2018

(30) Foreign Application Priority Data

Sep. 27, 2016 (JP) ................................. 2016-187870
Jul. 6, 2017 (JP) ................................. 2017-132513

(51) Int. Cl.
| | | |
|---|---|---|
| *C09D 11/322* | (2014.01) | |
| *C09D 11/328* | (2014.01) | |
| *C09D 11/06* | (2006.01) | |
| *C07C 229/24* | (2006.01) | |
| *C09B 62/04* | (2006.01) | |
| *D06P 1/647* | (2006.01) | |
| *D06P 5/30* | (2006.01) | |

(Continued)

(52) U.S. Cl.
CPC .......... *C09D 11/322* (2013.01); *C07C 229/24* (2013.01); *C09B 62/04* (2013.01); *C09D 11/06* (2013.01); *C09D 11/328* (2013.01); *C09D 11/38* (2013.01); *D06P 1/647* (2013.01); *D06P 5/30* (2013.01); *D06P 1/382* (2013.01); *D06P 1/39* (2013.01); *D06P 1/928* (2013.01)

(58) Field of Classification Search
None
See application file for complete search history.

(56) References Cited

U.S. PATENT DOCUMENTS 7,052,536 B2 * 5/2006 Yatake ................. C09D 11/322
106/31.33
7,344,236 B2   3/2008 Morimoto
(Continued)

FOREIGN PATENT DOCUMENTS

JP   2004-123904 A   4/2004
JP   2005-089591 A   4/2005
(Continued)

OTHER PUBLICATIONS

English translation of JP 2004/123904, Apr. 2004; 19 pages.*
(Continued)

*Primary Examiner* — Helene Klemanski
(74) *Attorney, Agent, or Firm* — Harness, Dickey & Pierce, P.L.C.

(57) ABSTRACT

An ink jet textile printing ink composition includes water; a color material; and a metal chelating agent. In the ink composition described above, the metal chelating agent includes at least one selected from methyl glycine diacetic acid, L-glutamate diacetic acid, L-aspartic diacetic acid, hydroxyethylimino diacetic acid, 3-hydroxy-2,2'-iminodisuccucinic acid, dicarboxymethyl glutamic acid, (S,S)-ethylenediaminedisuccinic acid, and salts thereof, and the pH of the ink composition is 6 to 10.

14 Claims, 3 Drawing Sheets

(51) Int. Cl.
  *C09D 11/38* (2014.01)
  *D06P 1/92* (2006.01)
  *D06P 1/39* (2006.01)
  *D06P 1/382* (2006.01)

(56) References Cited

U.S. PATENT DOCUMENTS

| | | | |
|---|---|---|---|
| 2004/0186200 A1 | 9/2004 | Yatake | |
| 2005/0057631 A1 | 3/2005 | Morimoto | |
| 2013/0115431 A1* | 5/2013 | Aoyama | C09D 11/322 428/195.1 |
| 2013/0213440 A1* | 8/2013 | Ohta | C09D 11/30 134/22.11 |
| 2014/0170395 A1* | 6/2014 | Kasperchik | C09D 11/106 428/204 |
| 2014/0287207 A1* | 9/2014 | Okuyama | B41J 2/01 428/207 |
| 2015/0259555 A1 | 9/2015 | Katoh et al. | |
| 2017/0247558 A1* | 8/2017 | Chen | C09D 11/322 |

FOREIGN PATENT DOCUMENTS

| | | | |
|---|---|---|---|
| JP | 2007-238798 A | | 9/2007 |
| JP | 2007/238892 A | * | 9/2007 |
| JP | 2008/266391 A | * | 11/2008 |
| JP | 2011/032413 A | * | 2/2011 |
| JP | 2011/032414 A | * | 2/2011 |
| JP | 2012-177079 A | | 9/2012 |
| JP | 2013-203850 A | | 10/2013 |
| JP | 2014-098122 A | | 5/2014 |
| JP | 2015-178624 A | | 10/2015 |

OTHER PUBLICATIONS

English translation of JP 2007/238892, Sep. 2007; 21 pages.*
English translation of JP 2008/266391, Nov. 2008; 15 pages.*
Extended European Search Report for Application No. EP 17 19 3333 dated Feb. 23, 2018 (9 pages).

* cited by examiner

INK JET TEXTILE PRINTING INK COMPOSITION AND INK RECEIVING CONTAINER

BACKGROUND

1. Technical Field

The present invention relates to an ink jet textile printing ink composition and an ink receiving container.

2. Related Art

An ink jet recording method is a printing method in which liquid droplets of an ink composition are ejected and flown from an ejection nozzle so as to be adhered to a recording medium, such as paper. This method is characterized in that an image having a high resolution and a high quality can be printed at a high rate using a relatively inexpensive apparatus. In an ink composition to be used for the ink jet recording method as described above, in accordance with a recording medium to be used, various color materials and solvents are used.

In textile printing fields, in response to request for shorter delivery time and high-variety low volume production, an ink jet textile printing method has been desired. When a dye is used for ink jet textile printing, besides the characteristics, such as color tone and washing fastness, which are the selection criteria for related textile printing dyes, in an ink jet recording method, for example, a dye solubility which realizes ejection stability from an ejection nozzle is restricted, and the dye selection is variously restricted. In addition, an ink jet textile printing ink composition is required not to cause clogging of an ejection nozzle by large size grains and the like and is also required, during manufacturing and/or storage of the ink composition, not to cause the change in physical characteristics of the ink composition, the precipitation of solid components thereof, and the like.

In addition, derived from a member with which an aqueous ink composition or its raw material thereof is brought into contact, metal ions and counter ions having a reactivity therewith may be present in some cases in the aqueous ink composition, and when those ions are precipitated therein by the formation of a metal salt having a poor water solubility, degradation in long-term storage property of the aqueous ink composition or generation of clogging at an ink jet head may arise in some cases. Hence, there has been known a technique of suppressing the precipitation of a metal salt by complexing metal ions using a chelating function (effect) of a metal chelating agent added to the aqueous ink composition or the like.

For example, JP-A-2005-89591 has proposed an ink jet textile printing ink which contains at least a dispersive dye, a dispersant, water, an aqueous organic solvent, and a polyvalent metal. In the textile printing ink described above, the dye solubility is prescribed, a predetermined amount of the polyvalent metal is contained, and the dispersive dye has a structure which is able to form a chelating compound with the polyvalent metal.

In addition, JP-A-2014-98122 has proposed an ink jet recording ink containing a metal chelating agent, such as sodium EDTA, tetrasodium EDTA, sodium picolinate, potassium quinolinate, or tetrasodium 3-hydroxy-2,2'-iminodisuccinate.

Furthermore, JP-A-2004-123904 has proposed an aqueous ink containing, for example, at least one selected from methyl glycine diacetic acid, L-glutamate diacetic acid, and salts thereof as a chelating agent.

SUMMARY

However, by the method disclosed in JP-A-2005-89591, the selection range of dyes is limited, and problems in that the chromogenic property and the fastness required for the textile printing ink are not satisfied may arise in some cases. In addition, by the chelating agents disclosed in JP-A-2014-98122 and JP-A-2004-123904, since the biodegradability is low, the environmental compatibility of the ink jet recording ink may not be satisfied in some cases, and/or since the chelating function is degraded dependent on the pH of the ink composition, the precipitation of a metal salt may not be suppressed in some cases, so that the degradation in long-term storage property of the ink composition and/or the clogging of the ink jet head are disadvantageously liable to occur.

In particular, the environmental compatibility has been considered to be important in recent printing business fields, and in commercial printing, the environmental compatibility represented by Eco Mark and/or NordicSwan has been considered to be important. In addition, in textile printing business fields, GOTS (Global Organic Textile Standard) has provided the standard for processing having a low environmental load or for chemical materials having a low environmental load, and recently, the product value has been substantially determined by the standard described above. As for the environmental load of the ink composition, in particular, the biodegradability is prescribed.

For example, some of reactive dyes to be used for textile printing may decrease the pH of the ink composition by hydrolysis. Hence, in order to minimize the occurrence of hydrolysis, the pH of the ink composition is required to be adjusted in an approximately neutral region. However, metal chelating agents have respective suitable pH ranges in each of which its chelating function is obtained. For example, although having biodegradability, the iminodisuccinic acid compound disclosed in JP-A-2014-98122 has a narrower pH range in which the chelating function is obtained than that of EDTA or the like. In addition, JP-A-2004-123904 has not disclosed a preferable pH range of the ink composition for the chelating agent (metal chelating agent).

The invention was made to solve at least some of the problems described above and can be realized as the following embodiments and application examples.

Application Example

An ink jet textile printing ink composition according to this application example comprises water, a color material, and a metal chelating agent, the metal chelating agent is at least one selected from methyl glycine diacetic acid (MGDA), L-glutamate diacetic acid (GLDA), L-aspartic diacetic acid (ASDA), hydroxyethylimino diacetic acid (HIDA), 3-hydroxy-2,2'-iminodisuccucinic acid (HIDS), dicarboxymethyl glutamic acid (CMGA), (S,S)-ethylenediaminedisuccinic acid (EDDS), and salts thereof, and the pH of the ink composition is 6 to 10.

According to this application example, a metal chelating agent having biodegradability is used, and hence, the environmental compatibility of the ink jet textile printing ink composition can be improved.

In addition, since the pH of the ink jet textile printing ink composition is set in the range described above, the degradation in chelating function (suppression of salt precipitation by the formation of a metal ion complex) of the metal chelating agent can be suppressed, and the chelating function can be preferably obtained as compared to that in the past. Hence, the long-term storage property of the ink jet textile printing ink composition can be improved, and in addition, the generation of clogging at an ink jet head can also be suppressed. That is, there can be provided an ink jet textile printing ink composition in which, compared to those in the past, the environmental compatibility and the long-term storage property are improved, and the generation of clogging is suppressed.

In the ink jet textile printing ink composition described in the application example described above, the content rate of the metal chelating agent with respect to the total mass of the ink composition is preferably 0.005 to 1.1 percent by mass.

Accordingly, the chelating function can be obtained, and at the same time, an excessive increase in viscosity of the ink jet textile printing ink composition caused by the addition of the metal chelating agent can be suppressed.

In the ink jet textile printing ink composition described in the application example described above, the ratio of the metal chelating agent to the color material is preferably 0.001:1 to 0.15:1.

Accordingly, the chelating function preferably works on a metal which may be unfavorably mixed in during a dye manufacturing process and/or a metal which is contained in a receiving container of the ink composition and which may be eluted thereinto, those metals each having a probability of forming a metal salt, so that generation of foreign materials causing the clogging of the ink jet head can be effectively suppressed. The ratio of the chelating agent to the color material is more preferably 0.003:1 to 0.085:1.

In the ink jet textile printing ink composition described in the application example described above, at least one selected from a pH buffer, an organic amine compound, and an inorganic compound is preferably contained.

Accordingly, the pH of the ink jet textile printing ink composition can be easily adjusted in the range described above. Hence, the chelating function of the metal chelating agent can be preferably obtained. In addition, for example, in an ink jet textile printing apparatus including an ink jet head, corrosion of members, such as an ink-repellent film, can be suppressed. Furthermore, the change in pH caused, for example, by the change in degree of hydrolysis with time can be suppressed.

In the ink jet textile printing ink composition described in the application example described above, the color material preferably has a halogenated triazine structure in its molecule.

Since a dye having a halogenated triazine structure is progressively hydrolyzed, in particular, when the dye is left alone, for example, the generation of foreign materials and the change in dyeing depth may disadvantageously occur when an ink composition is left alone for a long time. However, according to the ink composition of the application example described above, since the pH is set to 6 to 10, the hydrolysis of the dye is not likely to progress, and even after the ink composition is stored for a long time, textile printing can be performed on vegetable fibers, such as cotton, with stable dyeing conditions.

In the ink jet textile printing ink composition described in the application example described above, at least one selected from a glycol ether compound and a 1,2-alkanediol compound and at least one selected from a silicone compound, a fluorine compound, an acetylene glycol compound, and a poly(oxy ethylene) compound are preferably contained.

Accordingly, since at least one selected from a glycol ether compound and a 1,2-alkanediol compound is used, the wettability and the penetration rate of the ink jet textile printing ink composition to a recording medium, such as a cloth, are adjusted. Hence, an image, a pattern, and/or the like can be clearly textile-printed while being suppressed from oozing. In addition, since at least one selected from a silicone compound, a fluorine compound, an acetylene glycol compound, and a poly(oxy ethylene) compound is used, the surface tension of the ink jet textile printing ink composition is decreased, and hence, the wettability to a cloth or the like can be improved.

In the ink jet textile printing ink composition described in the application example described above, at least two types of solvents having a boiling point of 190° C. to less than 260° C. at one atmospheric pressure are preferably contained in an amount of 10 to 30 percent by mass with respect to the total mass of the ink composition; as the solvent, a nitrogen-containing heterocyclic compound and an alkylpolyol are preferably contained; and the content of the nitrogen-containing heterocyclic compound and the content of the alkylpolyol are each preferably 5 to 20 percent by mass with respect to the total mass of the ink composition.

Accordingly, by the use of the solvents described above, the wettability and the penetration rate of the ink jet textile printing ink composition to a recording medium, such as a cloth, can be adjusted. Hence, an image, a pattern, and/or the like can be clearly textile-printed while being suppressed from oozing.

The ink jet textile printing ink composition described in the application example described above is preferably received in an ink receiving container using a member containing a fatty acid compound.

Accordingly, in order to improve the physical properties, the quality, and the like, as an additive to a formation material of the member of the container used for the ink jet textile printing ink composition, a fatty acid compound (a fatty acid, a fatty acid salt, and/or a fatty acid ester) may be added. Since the metal chelating agent described above is contained, even when the ink jet textile printing ink composition is brought into contact with the member of the container, foreign materials, such as a metal salt, can be suppressed from being generated, for example, from a component of the additive. Hence, the long-term storage property of the ink jet textile printing ink composition can be improved, and the generation of clogging of the ink jet head can be suppressed.

Application Example

An ink receiving container according to this application example receives the ink jet textile printing ink composition described in the application example described above and uses a member containing a fatty acid compound.

According to this application example, since the metal chelating agent of the application example described above is contained, even when the member containing a fatty acid compound (a fatty acid, a fatty acid salt, and/or a fatty acid ester) and the ink jet textile printing ink composition are brought into contact with each other, foreign materials, such as a metal salt, are suppressed from being generated, for example, from a component of an additive. Hence, when the fatty acid compound is added as the additive to the member of the ink receiving container, the physical properties, the quality, and the like of the ink receiving container can be improved.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
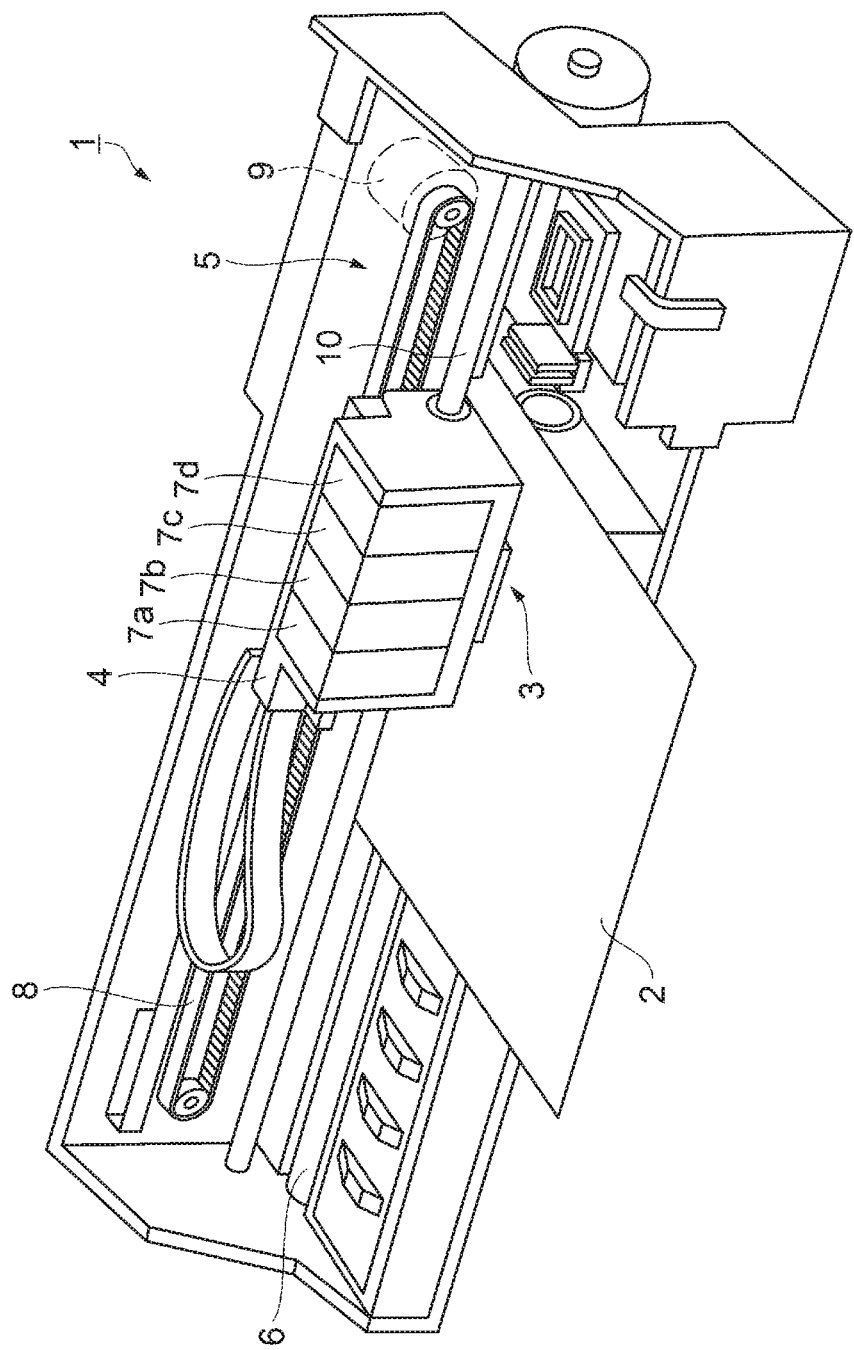
FIG. 1 is a schematic perspective view showing an ink jet textile printing apparatus according to an embodiment.

An ink jet textile printing ink composition (hereinafter, simply also referred to as "ink composition" in some cases) is ejected in the form of fine ink droplets (liquid droplets of the ink composition) to a recording medium, such as a cloth, through an ejection nozzle (hereinafter, simply also referred to as "nozzle" in some cases) of an ink jet head by an ink jet method and is formed into an image, a color, a letter, a pattern, and/or the like, so that the ink composition described above is used for textile printing application.

The ink jet textile printing ink composition according to this embodiment comprises water, a color material, and a metal chelating agent, the above metal chelating agent includes at least one of methyl glycine diacetic acid (MGDA), L-glutamine diacetic acid (GLDA), L-aspartic diacetic acid (ASDA), hydroxyethylimino diacetic acid (HIDA), 3-hydroxy-2,2'-iminodisuccinic acid (HIDS), dicarboxymethyl glutamic acid (CMGA), (S,S)-ethylenediaminedisuccinic acid (EDDS), and salts thereof, and the pH of the ink composition is 6 to 10. Hereinafter, individual components contained in the ink composition according to this embodiment will be described.

Water

Water functions as a primary solvent of the ink jet textile printing ink composition of this embodiment. When textile printing is performed, water is evaporated from a recording medium, such as a cloth, by drying. As the water, for example, there may be used purified water, such as ion exchanged water, ultrafiltered water, reverse osmosis water, or distilled water, or water, such as super pure water, from which ionic impurities are removed as much as possible. In addition, when water sterilized, for example, by irradiation of UV rays and/or by addition of hydrogen peroxide is used, in the case in which the ink composition is stored for a long time, the generation of mold and bacteria can be suppressed. Although the content of water contained in the ink composition is not particularly limited, with respect to the total mass of the ink composition, for example, the content is 45 percent by mass or more, preferably 50 to 95 percent by mass, and further preferably 55 to 90 percent by mass.

Color Material

As the color material, for example, in accordance with a formation material of a cloth on which textile printing is to be performed, a pigment or a dye is preferably used.

As the pigment, either a know organic pigment or a known inorganic pigment may be used. As the organic pigment, for example, there may be mentioned an azo pigment, such as an azo lake pigment, an insoluble azo pigment, a condensed azo pigment, or a chelate azo pigment; a polycyclic pigment, such as a phthalocyanine pigment, a perylene pigment, a perinone pigment, an anthraquinone pigment, a quinacridone pigment, a dioxazine pigment, a thioindigo pigment, an isoindolinone pigment, an isoindoline pigment, a quinophthalone pigment, or a diketopyrrolopyrrole pigment; a dye lake pigment, such as a basic dye lake or an acidic dye lake; a nitro pigment, a nitroso pigment, aniline black, or a daylight fluorescent pigment. As the inorganic pigment, for example, a metal oxide pigment, such as titanium dioxide, zinc oxide, or chromium oxide; or carbon black may be mentioned.

As the pigments mentioned above, for example, C.I. (Colour Index Generic Name) Pigment Black 1, 7, and 11 may be mentioned for a black ink composition. Among those mentioned above, for ink jet textile printing, a carbon black-based pigment (C.I. Pigment Black 7) which has a relatively low specific gravity and which is unlikely to precipitate in an aqueous solvent is preferable.

As a pigment to be used for a color ink composition, for example, there may be mentioned C.I. Pigment Yellow 1, 3, 12, 13, 14, 17, 24, 34, 35, 37, 42, 53, 55, 74, 81, 83, 95, 97, 98, 100, 101, 104, 108, 109, 110, 117, 120, 138, 153, 155, or 180; C.I. Pigment Red 1, 2, 3, 5, 17, 22, 23, 31, 38, 48:2 (Permanent Red"2B(Ba)), 48:2 (Permanent Red"2B(Ca)), 48:3, 48:4, 49:1, 52:2, 53:1, 57:1, 60:1, 63:1, 63:2, 64:1, 81, 83, 88, 101, 104, 105, 106, 108, 112, 114, 122, 123, 146, 149, 166, 168, 170, 172, 177, 178, 179, 185, 190, 193, 209, or 219; C.I. Pigment Violet 19 or 23; C.I. Pigment Blue 1, 2, 15, 15:1, 15:2, 15:3, 15:4, 15:6, 16, 17:1, 56, 60, or 63; or C.I. Pigment Green 1, 4, 7, 8, 10, 17, 18, or 36. The average grain diameter of the pigment is preferably 5 μm or less, more preferably 0.3 μm or less, and further preferably 0.01 to 0.15 μm. In this case, the "average grain diameter" indicates a volume-basis grain size distribution (50%) unless otherwise particularly noted. The average grain diameter is measured by a dynamic light scattering method or a laser diffraction light method, which are described in JIS Z8825. In particular, there may be used a grain size distribution meter (such as "Microtrack UPA" manufactured by Nikkiso Co., Ltd.) using a dynamic light scattering method as a measurement principle.

Although not particularly limited, for example, the content of the pigment with respect to the total mass of the ink composition is set to preferably 0.1 to 30 percent by mass, more preferably 1 to 20 percent by mass, and further preferably 1 to 15 percent by mass. Since the content of the pigment is set in the range described above, in a textile-printed product on which textile printing is performed, the coloring of the pigment is not only secured, but also the increase in viscosity of the ink composition and the generation of clogging of an ink jet head can be suppressed.

When the pigment is used as the color material, in order improve the dispersibility thereof in the ink composition, a surface treatment is preferably performed on the pigment, or a dispersant or the like is preferably added thereto. The surface treatment on the pigment is a method in which by a physical treatment or a chemical treatment, hydrophilic groups, such as a carboxyl group and/or a sulfonic group, are introduced on the grain surface of the pigment. By the surface treatment of the pigment, the pigment may be dispersed in a water-based solvent (aqueous solvent).

The dispersant to be used for an aqueous solvent has a function in which a hydrophobic portion (hydrophobic group) of a molecular structure adsorbs on the grain surface of the pigment, and a hydrophilic portion (hydrophilic group) is oriented to a solvent side (medium side). By this function, the pigment can be dispersed in an aqueous solvent. As the dispersant, at least one of known surfactants and resins may be used. In addition, a method in which the pigment grains are covered with a resin or the like so as to have the dispersibility may also be used. As a method for covering the pigment grains, for example, an acid precipitation method, a phase transfer emulsification method, or a mini-emulsion polymerization method may be used.

As the dye, for example, an aqueous dye, such as an acidic dye or a basic dye, a dispersive dye to be used together with a dispersant (surfactant), or a reactive dye may be mentioned. Since performing textile printing by dyeing through the formation of chemical bonds between functional groups of the formation material of a cloth and molecules of the dye, the dye is more preferably used as a color material for ink jet textile printing. When a dye appropriate for the formation material of a cloth is selected, compared to an ink composition using a pigment as the color material, the washing fastness and the friction resistance of a cloth (textile-printed product) on which textile printing is performed can be improved. Although the dye is not particularly limited, a known dye may be used.

In the ink composition of this embodiment, the color material (dye) preferably has a halogenated triazine structure in its molecule. Since a dye having a halogenated triazine structure is progressively hydrolyzed, in particular, when the dye is left alone, if a related ink composition is left alone for a long time, for example, the generation of foreign materials and the change in dyeing depth may disadvantageously occur in some cases. In the ink composition of this embodiment, since the pH is set to 6 to 10, the hydrolysis can be suppressed from progressing as compared to that in the past. Accordingly, even when the ink composition is stored for a long time, textile printing can be performed on vegetable fibers, such as cotton, with stable dyeing conditions.

Among dyes each having a halogenated triazine structure in its molecule, at least one selected from C.I. Reactive Blue 15, 15:1, and 49; C.I. Reactive Red 3, 3:1, 24, and 31; C.I. Reactive Yellow 2 and 95; C.I. Reactive Black 8 and 39; C.I. Reactive Orange 12 and 13; and C.I. Reactive Violet 1 is more preferably used. When the monochlorotriazine dye as described above is used, by the halogenated triazine structure, the dyeing conditions are stabilized, in particular, in vegetable fibers, such as cotton. Hence, the difference in hue between images or the like of textile-printed products formed from different cloths, such as vegetable fibers and animal fibers, can be reduced.

Although the reactive dye is not particularly limited, for example, there may be mentioned at least one selected from C.I. Reactive Blue 2, 3, 5, 7, 13, 14, 21, 25, 26, 38, 39, 40, 41, 46, 50, 69, 72, 109, 120, 143, and 176; C.I. Reactive Red 2, 4, 7, 12, 13, 14, 15, 16, 29, 32, 33, 43, 45, 46, 55, 58, 59, 79, 106, 111, 124, and 218; C.I. Reactive Yellow 3, 6, 7, 12, 15, 18, 22, 37, 42, 57, 69, 76, 81, 86, 102, 125, 135, and 181; C.I. Reactive Black 1, 3, 4, 5, 10, 12, 13, 14, 31, 34, and 35; Huntsman Black; C.I. Reactive Orange 2, 5, 20, and 99; C.I. Reactive Violet 1, 2, and 33; C.I. Reactive Green 5 and 8; and C.I. Reactive Brown 1, 2, 7, 8, 9, 11, and 14.

Although the dispersive dye is not particularly limited, for example, there may be mentioned C.I. Disperse Blue 3, 7, 9, 14, 16, 19, 20, 26, 27, 35, 43, 44, 54, 55, 56, 58, 60, 62, 64, 71, 72, 73, 75, 79, 81, 82, 83, 87, 91, 93, 94, 95, 96, 102, 106, 108, 112, 113, 115, 118, 120, 122, 125, 128, 130, 139, 141, 142, 143, 146, 148, 149, 153, 154, 158, 165, 167, 171, 173, 174, 176, 181, 183, 185, 186, 187, 189, 197, 198, 200, 201, 205, 207, 211, 214, 224, 225, 257, 259, 267, 268, 270, 284, 285, 287, 288, 291, 293, 295, 297, 301, 315, 330, and 333; C.I. Disperse Red 1, 4, 5, 7, 11, 12, 13, 15, 17, 27, 43, 44, 50, 52, 53, 54, 55, 56, 58, 59, 60, 65, 72, 73, 74, 75, 76, 78, 81, 82, 86, 88, 90, 91, 92, 93, 96, 103, 105, 106, 107, 108, 110, 111, 113, 117, 118, 121, 122, 126, 127, 128, 131, 132, 134, 135, 137, 143, 145, 146, 151, 152, 153, 154, 157, 159, 164, 167, 169, 177, 179, 181, 183, 184, 185, 188, 189, 190, 191, 192, 200, 201, 202, 203, 205, 206, 207, 210, 221, 224, 225, 227, 229, 239, 240, 257, 258, 277, 278, 279, 281, 288, 298, 302, 303, 310, 311, 312, 320, 324, and 328; C.I. Disperse Yellow 3, 4, 5, 7, 9, 13, 23, 24, 30, 33, 34, 42, 44, 49, 50, 51, 54, 56, 58, 60, 63, 64, 66, 68, 71, 74, 76, 79, 82, 83, 85, 86, 88, 90, 91, 93, 98, 99, 100, 104, 108, 114, 116, 118, 119, 122, 124, 126, 135, 140, 141, 149, 160, 162, 163, 164, 165, 179, 180, 182, 183, 184, 186, 192, 198, 199, 202, 204, 210, 211, 215, 216, 218, 224, 227, 231, and 232; C.I. Disperse Black 1, 3, 10, and 24; C.I. Disperse Orange 1, 3, 5, 7, 11, 13, 17, 20, 21, 25, 29, 30, 31, 32, 33, 37, 38, 42, 43, 44, 45, 46, 47, 48, 49, 50, 53, 54, 55, 56, 57, 58, 59, 61, 66, 71, 73, 76, 78, 80, 89, 90, 91, 93, 96, 97, 119, 127, 130, 139, and 142; C.I. Disperse Violet 1, 4, 8, 23, 26, 27, 28, 31, 33, 35, 36, 38, 40, 43, 46, 48, 50, 51, 52, 56, 57, 59, 61, 63, 69, and 77; C.I. Disperse Green 9; and C.I. Disperse Brown 1, 2, 4, 9, 13, and 19. In addition, the dispersive dye is preferably used together with a dispersant. As the dispersant, a known dispersant, such as a surfactant, may be used.

Although the acidic dye is not particularly limited, for example, there may be mentioned C.I. Acid Blue 1, 7, 9, 15, 22, 23, 25, 27, 29, 40, 41, 43, 45, 49, 54, 59, 60, 62, 72, 78, 80, 82, 83, 90, 92, 93, 100, 102, 103, 104, 112, 113, 117, 120, 126, 127, 129, 130, 131, 133, 138, 140, 142, 143, 151, 154, 158, 161, 166, 167, 168, 170, 171, 175, 182, 183, 184, 185, 187, 192, 199, 203, 204, 205, 225, 229, 234, 236, 247, 249, and 300; C.I. Acid Red 1, 6, 8, 9, 13, 14, 18, 19, 24, 26, 27, 28, 32, 35, 37, 42, 51, 52, 57, 62, 75, 77, 80, 82, 83, 85, 87, 88, 89, 92, 94, 95, 97, 106, 111, 114, 115, 117, 118, 119, 129, 130, 131, 133, 134, 138, 143, 145, 149, 154, 155, 158, 168, 180, 183, 184, 186, 194, 198, 199, 209, 211, 215, 216, 217, 219, 249, 252, 254, 256, 257, 260, 263, 265, 266, 274, 276, 282, 283, 303, 317, 318, 320, 321, 322, and 361; C.I. Acid Yellow 1, 3, 7, 11, 17, 19, 25, 29, 32, 36, 38, 40, 42, 44, 49, 59, 61, 70, 72, 75, 76, 78, 79, 98, 99, 110, 111, 112, 114, 116, 118, 119, 127, 128, 131, 135, 141, 142, 161, 162, 163, 164, 165, 169, 207, 219, and 246; C.I. Acid Black 1, 2, 7, 24, 26, 29, 31, 44, 48, 50, 51, 52, 58, 60, 62, 63, 64, 67, 72, 76, 77, 94, 107, 108, 109, 110, 112, 115, 118, 119, 121, 122, 131, 132, 139, 140, 155, 156, 157, 158, 159, 172, 191, and 234; C.I. Acid Orange 1, 7, 8, 10, 19, 20, 24, 28, 33, 41, 43, 45, 51, 56, 63, 64, 65, 67, 74, 80, 82, 85, 86, 87, 88, 95, 122, 123, and 124; C.I. Acid Violet 7, 11, 15, 31, 34, 35, 41, 43, 47, 48, 49, 51, 54, 66, 68, 75, 78, 97, and 106; C.I. Acid Green 3, 7, 9, 12, 16, 19, 20, 25, 27, 28, 35, 36, 40, 41, 43, 44, 48, 56, 57, 60, 61, 65, 73, 75, 76, 78, and 79; and C.I. Acid Brown 2, 4, 13, 14, 19, 20, 27, 28, 30, 31, 39, 44, 45, 46, 48, 53, 100, 101, 103, 104, 106, 160, 161, 165, 188, 224, 225, 226, 231, 232, 236, 247, 256, 257, 266, 268, 276, 277, 282, 289, 294, 295, 296, 297, 299, 300, 301, and 302.

As other dyes, for example, there may be mentioned C.I. Direct Blue 1, 2, 6, 9, 15, 22, 25, 41, 71, 76, 77, 78, 80, 86, 90, 98, 106, 108, 120, 123, 158, 160, 163, 165, 168, 192, 193, 194, 195, 196, 200, 201, 202, 203, 207, 225, 226, 236, 237, 246, 248, and 249; C.I. Direct Red 1, 2, 4, 9, 11, 13, 17, 20, 23, 24, 28, 31, 33, 37, 39, 44, 46, 62, 63, 75, 79, 80, 81, 83, 84, 89, 95, 99, 113, 197, 201, 218, 220, 224, 225, 226, 227, 228, 229, 230, and 231; C.I. Direct Yellow 1, 8, 11, 12, 24, 26, 33, 39, 44, 50, 58, 85, 86, 87, 88, 89, 98, 110, 132, 142, and 144; C.I. Direct Black 17, 19, 22, 32, 35, 38, 51, 56, 62, 71, 74, 75, 77, 94, 105, 106, 107, 108, 112, 113, 117, 118, 132, 133, 146, 154, 168, and 171; C.I. Solubilized Vat Blue 1, 5, and 41; C.I. Vat Blue 29; C.I. Food Blue 1 and 2; C.I. Basic Blue 9, 25, 28, 29, and 44; C.I. Solubilized Red 1; C.I. Food Red 7, 9, and 14; C.I. Food Yellow 3 and 4; C.I. Solubilized Vat Black 1; and C.I. Food Black 2.

As the color materials, the dyes mentioned above may be used alone, or at least two types thereof may be used in combination.

Although not particularly limited, for example, the content of the dye with respect to the total mass of the ink composition is preferably set to 0.5 to 30 percent by mass, more preferably 1 to 25 percent by mass, and further preferably 1 to 20 percent by mass. When the content of the dye is set in the range described above, the coloring of the dye can be secured in a textile-printed product, and at the same time, the increase in viscosity of the ink composition and the generation of clogging thereof can also be suppressed.

Metal Chelating Agent

The metal chelating agent has a chelating function (effect) of complexing a metal ion. By addition of the metal chelating agent to the ink composition, metal ions contained therein can be complexed. Hence, in the ink composition, precipitation of metal salts derived from a raw material and/or a member can be suppressed. In addition, the metal chelating agent has a suitable pH range in which the chelating function is obtained.

As the metal chelating agent, as described above, there may be used at least one chelating agent having biodegradability selected from methyl glycine diacetic acid (MGDA), L-glutamate diacetic acid (GLDA), L-aspartic diacetic acid (ASDA), hydroxyethylimino diacetic acid (HIDA), 3-hydroxy-2,2'-iminodisuccucinic acid (HIDS), dicarboxymethyl glutamic acid (CMGA), (S,S)-ethylenediaminedisuccinic acid (EDDS), and salts thereof. As the salts of the above metal chelating agents, for example, besides monovalent metal salts of sodium, potassium, lithium, and the like, salts of ammonium, an amine, and the like may also be mentioned.

Among the metal chelating agents described above, at least one of methyl glycine diacetic acid, trisodium methyl glycine diacetate, disodium methyl glycine diacetate, L-glutamate diacetic acid, tetrasodium L-glutamate diacetate, disodium L-glutamate diacetate, (S,S)-ethylenediaminedisuccinic acid, and trisodium (S,S)-ethylenediaminedisuccinate is more preferably used. In those metal chelating agents among all the metal chelating agents mentioned above, the degradation in chelating function with the change in pH of the ink composition is further suppressed. Hence, the chelating function can be obtained in a wider pH range, and for example, the response of the chelating function to the changed in pH of the ink composition, such as the change in pH with time, can be further improved.

In particular, when the ink composition uses as the color material, a color material having a halogenated triazine structure, the halogen contained in the color material may be eliminated in some cases, for example, by the change in degree of hydrolysis with time. Hence, the pH of the ink composition is liable to be remarkably changed, and since having a small pH range in which the chelating function is obtained, a related metal chelating agent is difficult to suppress the generation of foreign materials such as a metal salt. On the other hand, since having a wide pH range in which the chelating function is obtained as compared to that in the past, the more preferable metal chelating agent described above can be preferably used for an ink composition using a color material having a halogenated triazine structure.

The content rate (content) of the metal chelating agent with respect to the total mass of the ink composition is preferably 0.005 to 1.1 percent by mass, more preferably 0.005 to 0.5 percent by mass, and further preferably 0.01 to 0.3 percent by mass. When the content is 0.005 percent by mass or more, the chelating function can be effectively obtained, and when the content is 1.1 percent by mass or less, by the addition of the metal chelating agent, an excessive increase in viscosity of the ink composition and an excessive increase in pH thereof can be suppressed. In addition, in the ink composition, the ratio of the metal chelating agent to the color material is preferably in a range of from 0.001:1 to 0.15:1 (metal chelating agent/color material is 0.001 to 0.15), more preferably in a range of from 0.003:1 to 0.085:1, and further preferably in a range of from 0.01:1 to 0.07:1. As a material which may form a metal salt, there may be mentioned a metal which may be mixed in during a manufacturing process of the color material and/or a metal which is contained in an ink receiving container of the ink composition and which may be eluted therein; however, when the ratio of the metal chelating agent to the color material is set as described above, the generation of foreign materials which causes the clogging of the ink jet head can be effectively suppressed. In addition, the chelating function can be effectively obtained, and the excessive increase in viscosity of the ink composition and the excessive increase in pH thereof can be suppressed.

pH Adjuster

The ink jet textile printing ink composition of this embodiment preferably contains at least one selected from a pH buffer, an organic amine compound, and an inorganic alkali compound. Accordingly, the pH of the ink composition can be easily adjusted in a range of 6 to 10. Hence, the chelating function of the metal chelating agent can be preferably obtained. In addition, for example, in an ink jet textile printing apparatus including an ink jet head, corrosion of a member, such as an ink-repellent film, can be suppressed. Furthermore, the change in pH of the ink composition caused, for example, by the change in degree of hydrolysis with time can also be suppressed. In addition, in this specification, the pH buffer, the organic amine compound, and the organic alkali compound are collectively called a "pH adjuster".

As the pH buffer, for example, a phosphate buffer solution, a citric acid buffer solution, or a tris buffer solution may be mentioned. As the organic amine compound, for example, there may be mentioned triethanolamine, diethanolamine, monoethanolamine, tripropanolamine, triisopropanolamine, diisopropanolamine, trishydroxymethyl aminomethane, or N,N-bis(2-hydroxyethyl)-2-aminoethane sulfonic acid (BES). As the inorganic alkali compound, for example, a strong base which is a hydroxide of an alkali metal or an alkaline earth metal, such as lithium hydroxide, sodium hydroxide, potassium hydroxide, or calcium hydroxide, or ammonia may be mentioned. In addition, besides those compounds mentioned above, an inorganic acid, such as sulfuric acid, hydrochloric acid, or nitric acid, or an organic acid, such as adipic acid, citric acid, succinic acid, or lactic acid, may be used. The content of the pH adjuster with respect to the total mass of the ink composition is not particularly limited, and in accordance with a desired pH in a range of 6 to 10 of the ink composition, the pH may be arbitrarily adjusted. In particular, for example, when the inorganic alkali compound is added, the content thereof is preferably set in a range of 0.005 to 1 percent by mass with respect to the total mass of the ink composition.

Among those compounds mentioned above, triethanolamine, tripropanolamine, sodium hydroxide, potassium hydroxide, tris(hydroxymethyl)aminomethane, N,N-bis(2-hydroxyethyl)-2-aminoethane sulfonic acid, or adipic acid is more preferably used. Accordingly, the pH can be easily adjusted in a range of 6 to 10 during the manufacturing of the ink composition, and in addition, during a long-term storage thereof, the pH range described above can be easily retained.

Penetrating Agent

The ink jet textile printing ink composition of this embodiment preferably contains at least one selected from a glycol ether compound and a 1,2-alkanediol compound. In addition, in this specification, the glycol ether compound and the 1,2-alkanediol compound are collectively called a "penetrating agent". In addition, in this specification, the penetrating agent indicates a solvent, such as an organic solvent, having a property which enables the ink composition to easily penetrate into a recording medium, such as a cloth.

As the glycol ether compound, for example, an alkylene glycol monoether or an alkylene glycol diether may be mentioned.

As the alkylene glycol monoether, for example, there may be mentioned ethylene glycol monomethyl ether, ethylene glycol monoethyl ether, ethylene glycol monoisopropyl ether, ethylene glycol monobutyl ether, ethylene glycol monohexyl ether, ethylene glycol monophenyl ether, diethylene glycol monomethyl ether, diethylene glycol monoethyl ether, diethylene glycol monobutyl ether, diethylene glycol monohexyl ether, triethylene glycol monomethyl ether, triethylene glycol monoethyl ether, triethylene glycol monobutyl ether, tetraethylene glycol monomethyl ether, tetraethylene glycol monoethyl ether, propylene glycol monomethyl ether, propylene glycol monoethyl ether, dipropylene glycol monomethyl ether, dipropylene glycol monoethyl ether, or dipropylene glycol monopropyl ether.

As the alkylene glycol diether, for example, there may be mentioned ethylene glycol dimethyl ether, ethylene glycol diethyl ether, ethylene glycol dibutyl ether, diethylene glycol dimethyl ether, diethylene glycol diethyl ether, diethylene glycol methyl ethyl ether, diethylene glycol dibutyl ether, diethylene glycol butyl methyl ether, triethylene glycol dimethyl ether, triethylene glycol diethyl ether, triethylene glycol dibutyl ether, triethylene glycol butyl methyl ether, tetraethylene glycol dimethyl ether, tetraethylene glycol diethyl ether, tetraethylene glycol dibutyl ether, propylene glycol dimethyl ether, propylene glycol diethyl ether, dipropylene glycol dimethyl ether, or dipropylene glycol diethyl ether.

When the glycol ether compound is used, the content thereof with respect to the total mass of the ink composition is preferably 0.05 to 20 percent by mass, more preferably 0.1 to 20 percent by mass, and further preferably 1 to 15 percent by mass.

As the 1,2-alkanediol compound, for example, there may be mentioned 1,2-propanediol, 1,2-butanediol, 1,2-pentanediol, 1,2-hexanediol, or 1,2-octanediol. When the 1,2-alkanediol is used, the content thereof with respect to the total mass of the ink composition is preferably 0.5 to 15 percent by mass, more preferably 1 to 10 percent by mass, and further preferably 1 to 5 percent by mass.

Since a predetermined amount of the penetrating agent as described above is added to the ink composition, the wettability and the penetrating rate of the ink composition to a recording medium, such as a cloth, can be adjusted, so that an image, a pattern, and/or the like can be clearly textile-printed.

Surfactant

The ink jet textile printing ink composition of this embodiment preferably contains at least one selected from a silicone compound, a fluorine compound, an acetylene glycol compound, and a poly(oxy ethylene) compound. In addition, in this specification, the silicone compound, the fluorine compound, the acetylene glycol compound, and the poly(oxy ethylene) compound are collectively called a "surfactant".

Although the silicone compound is not particularly limited, a polysiloxane compound may be used. As the polysiloxane compound, for example, a polyether-modified organosiloxane may be mentioned. As a commercially available polyether-modified organosiloxane, for example, there may be mentioned BYK-306, BYK-307, BYK-333, BYK-341, BYK-345, BYK-346, BYK-347, BYK-348, or BYK-349 (trade name, manufactured by BYK); KF-351A, KF-352A, KF-353, KF-354L, KF-355A, KF-615A, KF-945, KF-640, KF-642, KF-643, KF-6020, X-22-4515, KF-6011, KF-6012, KF-6015, or KF-6017 (trade name, manufactured by Shin-Etsu Chemical Co., Ltd.); or Silface SAG002, 005, 503A, or 008 (trade name, manufactured by Nisshin Chemical Co., Ltd.).

Although the fluorine compound is not particularly limited, for example, there may be mentioned a perfluoroalkyl sulfonic acid salt, a perfluoroalkyl carboxylic acid salt, a perfluoroalkyl phosphoric acid ester, a perfluoroalkyl ethylene oxide adduct, a perfluoroalkyl betaine, a perfluoroalkyl amine oxide compound, or a fluorine-modified polymer. As a commercially available product of the compound mentioned above, for example, there may be mentioned S-144 or S-145 (trade name, manufactured by Asahi Glass Co., Ltd.); FC-170C, FC-430, or Fluorad FC4430 (trade name, manufactured by Sumitomo 3M Limited); FSO, FSO-100, FSN, FSN-100, or FSN-300 (trade name, manufactured by Dupont); FT-250 or FT-251 (trade name, manufactured by Neos Corp.); or BYK-340 (trade name, manufactured by BYK).

The acetylene glycol compound is not particularly limited, and for example, there may be mentioned Surfynol 104, 104E, 104H, 104A, 104BC, 104DPM, 104PA, 104PG-50, 104S, 420, 440, 465, 485, SE, SE-F, 504, 61, DF37, CT111, CT121, CT131, CT136, TG, GA, DF110D, Dynol 604, or 607 (trade name, manufactured by Air Products and Chemicals, Inc.); Olfine B, Y, P, A, STG, SPC, E1004, E1010, E1020, PD-001, PD-002W, PD-003, PD-004, PD-005, EXP.4001, EXP.4036, EXP.4051, EXP.4123, EXP.4200, EXP.4300, AF-103, AF-104, AK-02, SK-14, or AE-3 (trade name, manufactured by Nisshin Chemical Co., Ltd.), Acetylenol E00, E00P, E40, E60, or E100 (trade name, manufactured by Kawaken Fine Chemicals Co., Ltd.).

The poly(oxy ethylene) compound is not particularly limited, and for example, there may be mentioned Newcol No. 2300 series (such as 2303, 2327, or 2399-S), Newcol NT series (such as 3, 5, 7, or 9), Newcol No. 1000 series (such as 1004, 1006, 1008, 1203, 1305, or 1525)(trade name, manufactured by Nippon Nyukazai Co., Ltd.); Emulgen 102KG, 103, 104P, 105, 106, 108, 120, 147, 150, 220, 350, 404, 420, 705, 707, 709, 1108, 4085, or 2025G (trade name, manufactured by Kao Corp.); or a poly(oxy ethylene) alkyl ether compound, such as a poly(oxy ethylene)-poly(oxy propylene) hexyl ether ($C_6H_{13}$-EO—PO—OH).

The surfactants mentioned above may be used alone, or at least two types thereof may be used in combination. By the addition of the surfactant as mentioned above to the ink composition, while the ink composition is suppressed from being foamed, the surface tension of the ink composition can be decreased. Accordingly, the wettability of the ink composition to a recording medium, such as a cloth, is improved, and an image, a pattern, and/or the like can be clearly textile-printed thereon. The content of the surfactant with respect to the total mass of the ink composition is, for example, preferably 0.05 to 5 percent by mass, more preferably 0.1 to 5 percent by mass, and further preferably 0.2 to 4 percent by mass.

Solvent

The ink jet textile printing ink composition according to this embodiment preferably contains at least two types of solvents having a boiling point at one atmospheric pressure (normal boiling point) of 190° C. to less than 260° C., and the solvent preferably contains a nitrogen-containing heterocyclic compound and an alkylpolyol.

The normal boiling point of the solvent is required to be 190° C. to less than 260° C. and is preferably 210° C. to 250° C. Since the normal boiling point of the solvent is in the range described above, a preferable balance between a drying property and a moisture-retaining property of the ink composition is obtained, and the clogging of the ink jet head caused by drying can be suppressed. On the other hand, when the normal boiling point is less than 190° C., for example, although a recording rate of an image is advantageously improved due to a preferable drying property of the ink composition, the drying property of the ink composition adhered to the vicinity of the nozzle of the ink jet head is enhanced, and the clogging of the nozzle is liable to occur. In addition, when the normal boiling point of the solvent is 260° C. or more, although the ink composition adhered to the vicinity of the nozzle is suppressed from being dried, the viscosity of the ink composition is increased since the concentration thereof adhered to the vicinity of the nozzle is increased, and as a result, the clogging of the nozzle is liable to occur. Furthermore, when the normal boiling point of the solvent is 260° C. or more, since the solvent is not likely to be evaporated in a heat treatment step which will be described later and is liable to stay on a cloth, the dyeing of the dye is disturbed, and the color reproducibility of an image and the chromogenic property thereof are disadvantageously degraded in some cases.

The total mass of the solvents having a normal boiling point of 190° C. to less than 260° C. with respect to the total mass of the ink composition is preferably 10 to 30 percent by mass and more preferably 10 to 25 percent by mass. When the total mass of the solvents is in the range described above, the balance between the drying property and the moisture-retaining property of the ink composition tends to be further improved. Hence, a clogging recovery property is improved, and since the dyeing of the dye is suppressed from being disturbed, the color reproducibility of an image and the chromogenic property thereof are improved.

Nitrogen-Containing Heterocyclic Compound

A nitrogen-containing heterocyclic compound having a normal boiling point of 190° C. to less than 260° C. is excellent in solubility of the dye mentioned above and has a function to suppress solidification and drying of the ink composition.

As a particular example of the nitrogen-containing heterocyclic compound having a normal boiling point of 190° C. to less than 260° C., for example, N-methyl-2-pyrrolidone [204° C.], N-ethyl-2-pyrrolidone [212° C.], N-vinyl-2-pyrrolidone [193° C.], 2-pyrrolidone [245° C.], or 5-methyl-2-pyrrolidone [248° C.] may be mentioned. The value in the parentheses indicates the normal boiling point. Those nitrogen-containing heterocyclic compounds may be used alone, or at least two types thereof may be used in combination.

Although the content of the nitrogen-containing heterocyclic compound having a normal boiling point of 190° C. to less than 260° C. with respect to the total mass of the ink composition is required to be 5 to 20 percent by mass, the content is preferably 5 to 15 percent by mass. When the content of the nitrogen-containing heterocyclic compound is 5 percent by mass or more, the generation of clogging of the nozzle can be effectively suppressed, and when the content is 20 percent by mass or less, an image having preferable color reproducibility and chromogenic property can be obtained. On the other hand, when the content of the nitrogen-containing heterocyclic compound is less than 5 percent, the generation of clogging of the nozzle remarkably occurs.

Alkylpolyol

An alkylpolyol having a normal boiling point of 190° C. to less than 260° C. has a function of suppressing the solidification and drying of the ink composition.

As a particular example of the alkylpolyol having a normal boiling point of 190° C. to less than 260° C., for example, there may be mentioned 1,3-propanediol [210° C.], 1,3-butanediol [230° C.], 1,4-butanediol [230° C.], 1,5-pentanediol [242° C.], 1,6-hexanediol [250° C.], 2-ethyl-2-methyl-1,3-propanediol [226° C.], 2-methyl-2-propyl-1,3-propanediol [230° C.], 2-methyl-1,3-propanediol [214° C.], 2,2-dimethyl-1,3-propanediol [210° C.], 3-methyl-1,3-butanediol [203° C.], 2-ethyl-1,3-hexanediol [244° C.], 3-methyl-1,5-pentanediol [250° C.], 2-methyl-pentane-2,4-diol [197° C.], diethylene glycol [245° C.], or dipropylene glycol [232° C.]. In addition, the value in the parentheses indicates the normal boiling point. Those alkylpolyols mentioned above may be used alone, or at least two types thereof may be used in combination.

Although the content of the alkylpolyol having a normal boiling point of 190° C. to less than 260° C. with respect to the total mass of the ink composition is required to be 5 to 20 percent by mass, the content is preferably 5 to 15 percent by mass. When the content of the alkylpolyol is 5 percent by mass or more, the generation of clogging of the nozzle can be effectively suppressed, and when the content is 20 percent by mass or less, an image having preferable color reproducibility and chromogenic property can be obtained. On the other hand, when the content of the alkylpolyol is less than 5 percent by mass, the generation of clogging of the nozzle remarkably occurs.

Other Components

To the ink jet textile printing ink composition of this embodiment, besides the components described above, various additives, such as a moisture-retaining agent, an antiseptic agent, a fungicide, a corrosion inhibitor, a dissolution auxiliary agent, a viscosity adjuster, a light stabilizer, an UV absorber, a resin emulsion, and/or a cross-linking agent may be appropriately added.

An urea functions as a moisture-retaining agent of the ink composition or a dyeing auxiliary agent improving a dyeing property of a dye. As a particular example of the urea, for example, urea, ethyleneurea, tetramethylurea, thiourea, or 1,3-dimethyl-2-imidazolidinone may be mentioned. When an urea is contained, the content thereof with respect to the total mass of the ink composition may be set to 1 to 20 percent by mass.

When a fungicide and/or an antiseptic agent is added to the ink composition, bacteria and/or mold is suppressed from breeding in the ink composition. As the fungicide and the antiseptic agent, for example, there may be mentioned sodium benzoate, sodium pentachlorophenol, sodium 2-pyridinethiol-1-oxide, sodium sorbate, sodium dehydroacetate, or 1,2-benzisothiazoline-3-one (trade name: Proxel CRL, Proxel BDN, Proxel GXL, Proxel XL-2, or Proxel TN, manufactured by LONZA). When the antiseptic agent or the fungicide is added, the content thereof with respect to the total mass of the ink composition is preferably 0.05 to 1 percent by mass.

By addition of the corrosion inhibitor to the ink composition, a metal member with which the ink composition is brought into contact can be suppressed from being corroded. As the corrosion inhibitor, a benzotriazole compound, such as 1,2,3-benzotriazole or carboxybenzotriazole, may be mentioned. When the corrosion inhibitor is added, the content thereof with respect to the total mass of the ink composition is preferably 0.001 to 0.5 percent by mass.

Ink Jet Textile Printing Ink Composition

The ink jet textile printing ink composition of this embodiment may be prepared in such a way that the components described above are mixed together in an arbitrary order, and if needed, impurities, foreign materials, and the like are then removed by filtration or the like. As a method for mixing the components, there may be used a method in which materials are sequentially charged into a container having a stirring device, such as a mechanical stirrer or a magnetic stirrer, and are then stirred and mixed together. As a filtration method, for example, centrifugal filtration or filter filtration may be used.

The surface tension of the ink composition at 25° C. is preferably 10 to 40 mN/n, more preferably 20 to 40 nmN/m, and further preferably 20 to 35 mN/m. Since the surface tension at 25° C. is set in the range described above, when textile printing is performed by an ink jet method, ejection stability of the ink composition from an ink jet head can be improved. In addition, for example, a highly fine image can be formed on a recording medium to be textile-printed. In addition, the surface tension of the ink composition can be measured using an automatic surface tension meter CBVP-Z (manufactured by Kyowa Interface Science Co., Ltd.). In particular, in an environment at 25° C., the surface tension may be obtained by measurement performed in such a way that a platinum plate is partially dipped in the ink composition.

As is the case of the surface tension, the viscosity of the ink composition at 20° C. is preferably 2 to 15 mPa·s (millipascal·sec), more preferably 2 to 10 mPa·s, and further preferably 3 to 6 mPa·s. In addition, the viscosity of the ink composition can be measured using a viscoelasticity tester MCR-300 (manufactured by Pysica Co., Ltd.). In particular, the viscosity can be obtained in such a way that after the temperature of the ink composition is set to 20° C., the shear rate is increased from 10 to 1,000, and a viscosity at a shear rate of 200 is measured.

The pH of the ink composition is set in a range of 6 to 10, more preferably 6.5 to 10, and further preferably 7 to 10. In addition, from immediately after the manufacturing of the ink composition and to a period of the storage thereof, the pH is preferably retained in the range described above. Accordingly, the chelating function of the metal chelating agent can be preferably obtained. In addition, accordingly, since the corrosive property of the ink composition is suppressed, for example, in an ink jet textile printing apparatus including an ink jet head, the member, such as the ink-repellent film, can be suppressed from being corroded. Furthermore, the change in pH of the ink composition with time can be suppressed. In this embodiment, "immediately after the manufacturing" indicates 24 hours or less from the blending of the components of the ink composition, and "to the period of the storage" indicates a period from filling of the ink composition in an ink receiving container, such as an ink cartridge, to ejection of the ink composition from an ink jet head. For example, the storage period may indicate a product warranty period of the ink cartridge in some cases. The pH of the ink composition may be adjusted using the pH adjuster described above. In addition, an acceleration test may be performed by a high-temperature storage at approximately 60° C. so that the pH value during the storage is estimated.

The ink composition may be prepared using at least one of the color materials described above. Ink compositions exhibiting different color tones in a textile-printed product are received in respective ink receiving containers, and those containers may be used in combination as an ink set of ink jet textile printing ink compositions.

Ink Jet Textile Printing Apparatus

An ink jet textile printing apparatus according to this embodiment will be described with reference to FIG. 1. The ink jet textile printing apparatus is an apparatus which performs textile printing by landing ink droplets on a cloth or the like using an ink jet method. FIG. 1 is a schematic perspective view showing the ink jet textile printing apparatus according to this embodiment. In this embodiment, as the ink jet textile printing apparatus, an on-carriage type printer in which ink cartridges are mounted on a carriage will be described by way of example. In addition, in FIG. 1, in order to enable individual members to be visually recognized, the scale of each member is set different from the actual value.

A printer 1 as the ink jet textile printing apparatus is a so-called serial printer. The serial printer is a printer in which a head is mounted on a carriage configured to move in a predetermined direction, and printing is performed while the head is moved in association with the movement of the carriage.

The printer 1 includes, as shown in FIG. 1, a head functioning as an ink jet head, a carriage 4, a main scanning mechanism 5, a platen roller 6, and a control portion (not shown) controlling the operation of the entire printer 1. The carriage 4 mounts the head 3 and also can detachably mount ink cartridges 7a, 7b, 7c, and 7d each functioning as an ink receiving container in which an ink composition to be supplied to the head 3 is received.

The main scanning mechanism 5 includes a timing belt 8 connected to the carriage 4, a motor 9 driving the timing belt 8, and a guide shaft 10. The guide shaft 10 is provided as a support member of the carriage 4 along a scanning direction (main scanning direction) thereof. The carriage 4 is driven by the motor 9 with the timing belt 8 provided therebetween so as to reciprocate along the guide shaft 10. Accordingly, the main scanning mechanism 5 has a function of reciprocating the carriage 4 in the main scanning direction.

The platen roller 6 has a function to transport a recording medium 2, such as a cloth, to be textile-printed in a sub-scanning direction (longitudinal direction of the recording medium 2) orthogonal to the main scanning direction described above. Hence, the recording medium 2 is transported in the sub-scanning direction. In addition, the carriage 4 on which the head 3 is mounted is able to reciprocate in the main scanning direction which is approximately coincides with the width direction of the recording medium 2, and the head 3 is able to be scanned in the main scanning direction and the sub-scanning direction relatively to the recording medium 2.

The ink cartridges 7a, 7b, 7c, and 7d are four ink cartridges (ink receiving containers) independent from each other. In each of the ink cartridges 7a, 7b, 7c, and 7d, the ink composition described above can be received. In those ink cartridges, ink compositions exhibiting colors, such as black, cyan, magenta, and yellow, are respectively received and may be arbitrarily used in combination as an ink set. In FIG. 1, although the number of the ink cartridges is four, the number is not limited thereto. In each of bottom portions of the ink cartridges 7a, 7b, 7c, and 7d, a supply port (not shown) supplying the ink composition received in each ink cartridge to the head 3 is provided.

In addition, the ink jet textile printing ink composition of this embodiment is preferably received in an ink receiving container formed of a member which suppresses moisture evaporation and in which the ink composition is not likely to be deteriorated. In this embodiment, as the ink receiving container, although the ink cartridges 7a, 7b, 7c, and 7d are describe by way of example, the ink receiving container is not limited thereto. As the ink receiving container in which the ink composition is to be received, besides the ink cartridge, for example, an ink pack or an ink bottle may also be used. Although a formation material of the ink receiving container is not particularly limited, a material which is not likely to be degraded by the ink composition and which has characteristics, such as physical properties, unlikely to be changed is preferably used. For example, in view of easy processing, light weight, and the like, a resin is preferably used.

A resin member is manufactured, for example, by rolling or injection molding in some cases, and in order to improve the processability and the yield in the manufacturing process, a mold-releasing agent may be used in some cases. In addition, in order to improve the physical properties of the member, additives, such as a lubricant and/or a plasticizer, may also be added to the formation material in some cases. As the additives described above, for example, a fluorine compound, a silicone compound, and/or a fatty acid compound may be mentioned. In addition, in this specification, a fatty acid, a fatty acid salt (metal salt), and a fatty acid ester are collectively called a "fatty acid compound".

In particular, the fatty acid compound has been used for versatile purposes, and in particular, a fatty acid, such as stearic acid, lauric acid, or ricinoleic acid, or its metal salt (fatty acid salt) has been widely used. However, when eluted into the ink composition, those compounds may be contained in the ink composition as impurities, or those compounds may generate in some cases, foreign materials as poor water soluble metal salts by a reaction with metal ions of lithium, magnesium, calcium, barium, zinc, and/or the like which are eluted into the ink composition from other members. In the past, although countermeasures have been investigated, for example, by reduction of the amount of the additives for ink jet application, in consideration of the performance as the ink receiving container, the cost thereof, and the like, the problems cannot be sufficiently solved only by the resin member.

On the other hand, since the ink composition of this embodiment contains the metal chelating agent, the generation of foreign materials described above can be suppressed, so that the ink jet textile printing ink composition of this embodiment is preferably contained in an ink receiving container using a member containing a fatty acid compound. In particular, even when the ink composition is received in an ink receiving container containing a member having a metal salt, impurities of the ink composition and eluted metal ions are trapped by the metal chelating agent, and the generation of foreign materials is suppressed. Hence, a member in which the processability and the physical properties are improved by addition of the additives may be used as the ink receiving container. In addition, for example, in the manufacturing process of the ink receiving container, when the fatty acid compound is used as a sub-component, such as a mold-releasing agent, the yield and the quality can be improved. That is, the ink receiving container of this embodiment is preferably an ink receiving container which receives the ink composition of this embodiment and which uses a member containing a fatty acid compound.

The head 3 has a nozzle surface (not shown) facing the recording medium 2. On the nozzle surface, for example, a high molecular weight film containing a fluorine compound and a silicone compound or a co-precipitated plating film containing a nickel and a fluorine compound may be formed as an ink-repellent film. In addition, on the nozzle surface, nozzle lines (not shown) formed of a plurality of nozzles (not shown) are disposed for respective color ink compositions. The color ink compositions are supplied to the head 3 from the ink cartridges 7a, 7b, 7c, and 7d and are each ejected in the form of liquid droplets from the nozzle by an actuator (not shown) disposed in the head 3. The ink droplets thus ejected are landed on the recording medium 2, so that an image, a color, a letter, a pattern, and/or the like are formed thereon.

In this case, in the head 3, as the actuator (driving device), although a piezoelectric element is used, the actuator is not limited thereto. For example, as the actuator, an electro-mechanical conversion element in which a vibration plate is displaced by electrostatic adsorption or an electro-thermal conversion element in which liquid droplets of an ink composition is ejected by air bubbles generated by heating may also be used.

In addition, in this embodiment, as the ink jet textile printing apparatus, although the on-carriage type printer 1 has been described by way of example, the ink jet textile printing apparatus is not limited thereto. For example, an off-carriage type printer in which an ink receiving container, such as an ink cartridge, is not mounted on a carriage, may also be used. In addition, the ink jet textile printing apparatus used in the invention is not limited to the above serial type printer and may be a line-head printer in which a head having a width equal to or larger than that of the recording medium 2 is disposed, and textile printing is performed without moving the head.

Although the recording medium 2 is not particularly limited as long as textile printing can be performed thereon with the ink composition, a cloth is preferably used. As a formation material of the cloth, for example, there may be mentioned vegetable fibers, such as cotton, hemp, or the like; animals fibers, such as silk, sheep wool, or the like; synthetic fibers, such as a nylon, a polyester, an acetate, a triacetate, a polyurethane, or the like; and biodegradable fibers, such as a poly(lactic acid) or the like. As the form of cloth, for example, a woven cloth, a knitted cloth, or a nonwoven cloth, which is formed from single-component fibers or blended fibers containing at least one of the above formation materials, may be mentioned, and in addition, clothing, other clothing ornaments, and the like formed from the above cloths may also be mentioned. In particular, besides sewn products including a T shirt, a handkerchief, a scarf, a towel, a handbag, a cloth-made bag, a curtain, a sheet, a bed cover, furniture, such as wallpaper, and a display, such as a cloth-made sign board or a banner, as a pre-sewn product, for example, fabric before and after cutting may also be mentioned. As the form of fabric, for example, a long fabric wound in the form of a roll, a fabric having a predetermined size by cutting, and a fabric having a product shape may be mentioned.

The color material used for the ink composition is preferably selected in consideration of the compatibility with the formation material of the cloth. For example, although the color material is not particularly limited, an acidic dye is preferably used for sheep wool, a nylon, silk, and the like; a dispersive dye is preferably used for a polyester, an acetate, a nylon, and the like; and a reactive dye is preferably used for cotton, hemp, rayon, silk, and the like. In addition, although not particularly limited by the type of cloth, a pigment may be primarily used for cotton.

In addition, although not particularly limited, the weight per unit area of the cloth is 1.0 to 10.0 oz (ounce), preferably 2.0 to 9.0 oz, more preferably 3.0 to 8.0, and further preferably 4.0 to 7.0 oz.

Textile Printing Method

Next, an ink jet textile printing method using the ink composition of this embodiment and the above printer 1 (see FIG. 1) will be described. The textile printing method of this embodiment includes a step of applying the ink composition. In addition, as a pre-step, a pre-treatment step of applying a pre-treatment liquid onto a cloth (recording medium 2) may be provided. As the pre-treatment liquid, for example, there may be used a liquid of assisting or changing the behavior, such as penetration and/or drying, of the ink composition applied onto the cloth or a liquid having a reactivity with the ink composition to improve the chromogenic property, the friction fastness, and/or the like. As a method for applying the pre-treatment liquid, for example, there may be mentioned an immersion method, a spray method, or an ink jet method. In addition, as a post-step, for example, a heating step, a washing step, and/or a drying step for the cloth may also be provided.

In the step of applying the ink composition, ink droplets are applied from the head 3 of the printer 1 onto the cloth. In this case, the ink droplets each having a predetermined volume (mass) are intermittently ejected at a predetermined timing and are adhered to the cloth, so that a design having desired image, letter, pattern, color, and/or the like is formed (textile-printed).

The adhesion amount of the ink composition to the cloth is preferably 1.5 to 6 mg/cm$^2$ and more preferably 2 to 5 mg/cm$^2$. When the adhesion amount is 1.5 mg/cm$^2$ or more, the coloring of an image or the like to be textile-printed tends to be improved. In addition, when the adhesion amount is 6 mg/cm$^2$ or less, the drying property of the ink droplets on the cloth is improved, and oozing is suppressed from being generated in a textile-printed image or the like.

In a step of heating the cloth, the ink composition applied onto the cloth is heated. The heating step is performed to dry the ink droplets, and in addition, when a dye is used as the color material, this heating step is also performed to fix the dye to the formation material of the cloth (dyeing). Although a heating method used in the heating step is not particularly limited, for example, there may be mentioned a heat press method, a normal pressure steam method, a high pressure steam method, or a thermofixing method. In addition, although a heat source of the heating is not particularly limited, for example, infrared rays (lamp) may be mentioned.

Although not particularly limited, a heating temperature in the heating step is preferably 100° C. to 200° C. and more preferably 150° C. to 180° C. When the heating temperature is set in the range as described above, a thermal damage on the cloth can be reduced, and the drying and the fixing of the ink composition can be promoted. In addition, the heating temperature described above indicates a surface temperature of a design, such as an image, formed on the cloth and may be measured, for example, by a non-contact type thermometer IT2-80 (trade name, manufactured by Keyence Corp.).

In addition, although not particularly limited, for example, a heating time of applying the heating temperature may be set to 30 seconds to 20 minutes.

In the washing and the drying steps, the cloth on which textile printing is performed is washed with water and dried. In the water washing, if needed, as a soaping treatment, for example, a dye which is not dyed in the cloth and/or a pigment which is not fixed in the cloth may be removed by washing using a hot soap liquid or the like.

As described above, according to the ink jet textile printing ink composition and the ink receiving container of this embodiment, the following effects can be obtained. Since the metal chelating agent having biodegradability is used, the environmental compatibility of the ink composition can be improved as compared to that in the past.

Since the pH of the ink composition is set in the range described above, the degradation in chelating function of the metal chelating agent can be suppressed, and the chelating function can be preferably obtained as compared to that in the past. Hence, the long-term storage property of the ink composition can be improved compared to that in the past, and the generation of clogging at the ink jet head can be suppressed as compared to that in the past. In particular, in industrial applications, such as textile printing, compared to general household applications and office applications, a large amount of ink compositions is consumed. Hence, when the generation of foreign materials is suppressed, the ink jet textile printing apparatus can be stably operated as compared to that in the past. Accordingly, the amount of waste generated in a textile-printing step is reduced, and the environmental compatibility is further improved.

By the use of the pH adjuster described above, the pH of the ink composition can be easily adjusted in the range described above. Hence, the chelating function of the metal chelating agent can be preferably obtained. In addition, even when a color material, such as a reactive dye, is used which decreases the pH of the ink composition by hydrolysis, by the adjustment of the pH of the ink composition, the occurrence of hydrolysis can be suppressed.

By the use of the color material described above, when textile printing is performed on the cloth, a clear textile-printed product having a high chromogenic property can be obtained. In addition, the light resistance, the washing fastness, and the friction resistance of a textile-printed product can be improved.

By the use of the penetrating agent and the surfactant described above, the wettability and the penetrating rate of the ink composition to a recording medium, such as a cloth, can be adjusted. Hence, an image, a pattern, and/or the like can be clearly textile-printed while oozing is suppressed.

Since the metal chelating agent of this embodiment is contained, even when the member containing a fatty acid compound and the ink composition are brought into contact with each other, foreign materials, such as a metal salt, are suppressed from being generated, for example, from the components of the additives and the sub-components. Hence, when the fatty acid compound is added to the member of the ink receiving container as the additive or is used as the sub-component in the manufacturing process, for example, the physical properties and the quality of the ink receiving container can be improved.

Accordingly, there can be provided an ink jet textile printing ink composition which has improved environmental compatibility and long-term storage property, which improves the image quality of a textile-printed product, and which suppresses the generation of clogging.

Hereinafter, as for the metal chelating agent and the ink composition of this embodiment, examples and comparative examples will be described in each of which the pH dependence of the chelating function, the storage stability (change in physical properties, generation of foreign materials, and change in chromogenic property) as the long-term storage property, the biodegradability, the clogging recovery property of the nozzle, and the corrosion of the ink-repellent film are evaluated, and the effect of this embodiment will be more particularly described.

Chelating Function

From a titration amount by neutralization titration and the change in pH, a metal ion trapping rate (pH dependence) of the metal chelating agent at each pH was investigated, and the chelating function was evaluated. As examples, three types, that is, MGDA·3Na (trisodium methyl glycine diacetate), GLDA·4Na (tetrasodium L-glutamate diacetate), and EDDS·3Na (trisodium (S,S)-ethylenediaminedisuccinate), were used. As comparative examples, two types, that is, EDTA·2Na (disodium ethylenediaminetetraacetate) which had a relatively low biodegradability and IDS·4Na (tetrasodium iminodisuccinate) which was estimated to have a high pH dependence although having biodegradability, were used.

First, a neutralization titration curve of each of an aqueous solution A containing only the metal chelating agent and an aqueous solution B containing the metal chelating agent and calcium ions ($Ca^{2+}$) at an equivalent molar ratio were formed. From the two neutralization titration curves of the aqueous solution A and the aqueous solution B, an intersection at a low pH side and an intersection at a high pH side were assumed to be a $Ca^{2+}$ trapping rate of 0% and a $Ca^{2+}$ trapping rate of 100%, respectively. Next, the neutralization titration curve of the aqueous solution B was plotted in such a way that the horizontal line and the vertical line represented the pH and the $Ca^{2+}$ trapping rate, respectively. By the method described above, a graph showing the $Ca^{2+}$ trapping rate with respect to the pH, that is, the pH dependence of the $Ca^{2+}$ trapping rate, was obtained.

Next, a particular procedure will be described using MGDA.3Na of the example. First, an aqueous solution of MGDA.3Na having a concentration of $2.5 \times 10^2$ mol/L was formed. The aqueous solution of MGDA.3Na having a concentration of $2.5 \times 10^{-2}$ mol/L was diluted with super pure water having a volume two times that thereof, so that the aqueous solution A was prepared. The aqueous solution of MGDA.3Na having a concentration of $2.5 \times 10^{-2}$ mol/L and a calcium standard liquid (Ca: 1,000 mg/L) (mixed aqueous solution containing 0.25 percent by mass of calcium carbonate and 0.63 percent by mass of nitric acid, manufactured by Wako Pure Chemicals Industries, Ltd.) were mixed and stirred together at an equivalent mass ratio, so that the aqueous solution B was prepared. In addition, in this embodiment, as the water, super pure water having an electrical resistivity of 17 MΩ·cm or more was used.

Next, the neutralization titration curve of each of the aqueous solution A and the aqueous solution B was obtained by titration. As a titration device, an automatic titration device COM1700E (manufactured by Hiranuma Sangyo Co., Ltd.) was used, and the titration was performed using an acid (hydrochloric acid at a concentration of 1 mol/L) or a base (sodium hydroxide aqueous solution at a concentration of 1 mol/L). Since the initial pH of the aqueous solution A was approximately 11, after the pH was decreased to approximately 2 by the titration with the acid, the titration was performed with the base. Since the initial pH of the aqueous solution B was approximately 2, the titration was performed with the base. The data thus obtained was shown in FIG. 2. In addition, although the titration with the base was started from a pH of approximately 2, the point at a pH of 3.5 was regarded as a starting point of the base titration amount.

Figure 2:
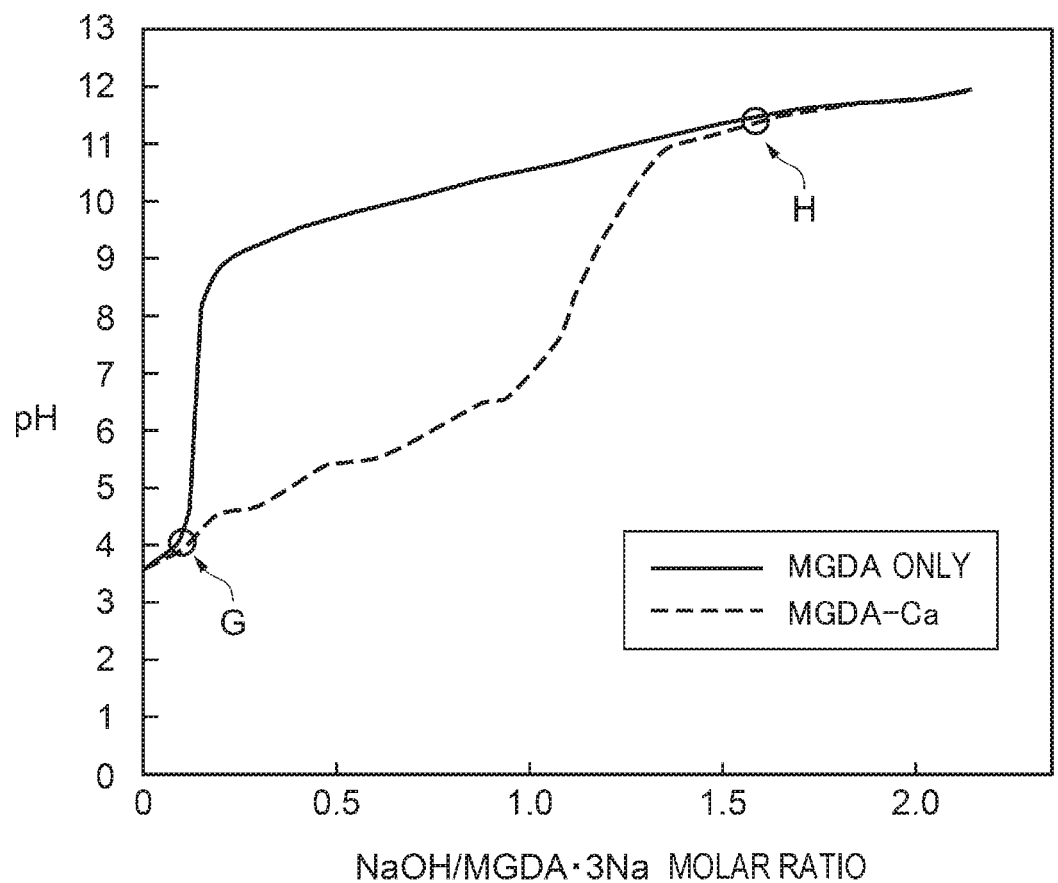
FIG. 2 is a graph showing neutralization titration curves of MGDA.3Na.

FIG. 2 is a graph showing the neutralization titration curve of MGDA.3Na. In FIG. 2, the horizontal axis represents the molar ratio of NaOH (sodium hydroxide)/MGDA.3Na calculated from the base titration amount, the vertical axis represents the pH corresponding to the molar ratio described above, and the measurement points are connected to each other. The solid line represents the neutralization titration curve of the aqueous solution A, and the dotted line represents the neutralization titration curve of the aqueous solution B. In addition, in a pH range of from 2 to 12, no precipitation of MGDA occurred.

As shown in FIG. 2, the intersection of the above two neutralization titration curves at a low pH side was represented by a point G, and the intersection thereof at a high pH side was represented by a point H. As described above, the point G and the point H were assumed as a $Ca^{2+}$ trapping rate of 0% and a $Ca^{2+}$ trapping rate of 100%, respectively, of MGDA.3Na. Next, the molar ratio of NaOH/MGDA.3Na from the point G to the point H was regarded as the $Ca^{2+}$ trapping rate, and a curve segment from a $Ca^{2+}$ trapping rate of 0% to a $Ca^{2+}$ trapping rate of 100% was equally divided. Next, the neutralization titration curve of the aqueous solution B was re-plotted so that the horizontal axis represented the pH, and the vertical axis represented the $Ca^{2+}$ trapping rate. By the method described above, a graph showing the pH dependence of the $Ca^{2+}$ trapping rate of MGDA.3Na was obtained. As for the GLDA.4Na, EDDS.3Na, EDTA.2Na, and IDS.4Na, the graph of the pH dependence of the $Ca^{2+}$ trapping rate could also be obtained in a manner similar to that described above. The results are shown in FIG. 3.

Figure 3:
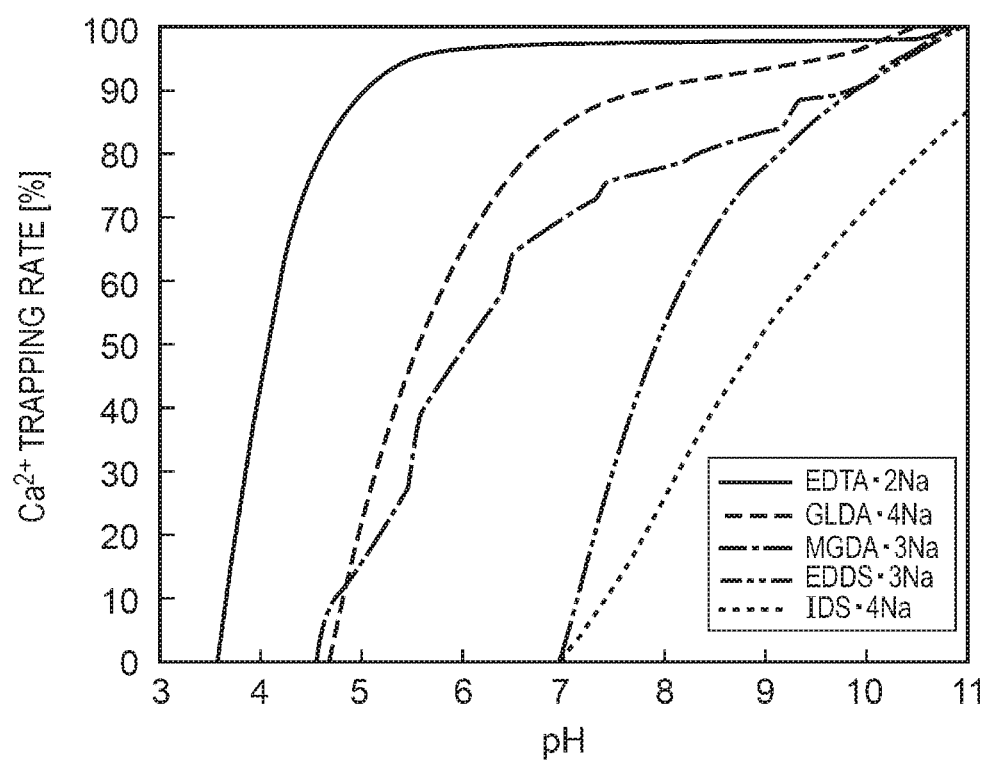
FIG. 3 is a graph showing the pH dependences of $Ca^{2+}$ trapping rates of examples and comparative examples.

FIG. 3 is a graph showing the pH dependence of the $Ca^{2+}$ trapping rate of each of the examples and the comparative examples. As shown in FIG. 3, as for GLDA.4Na and MGDA.3Na of the examples, in a pH range of 6 to 10, the $Ca^{2+}$ trapping rate is approximately 50% or more, and a preferable chelating function is shown. In addition, as for EDDS.3Na of the example, although the pH is required to be approximately 8 or more in order to secure a $Ca^{2+}$ trapping rate of 50%, a high chelating function is shown as compared to that of IDS.4Na of the comparative example.

On the other hand, it was found that in a wide pH range as compared to that of GLDA.4Na and MGDA.3Na of the examples, EDTA.2Na of the comparative example had a preferable chelating function. In addition, it was also found that IDS.4Na of the comparative example had a low $Ca^{2+}$ trapping rate and an inferior chelating function as compared to those of each of the three metal chelating agents of the examples.

Preparation of Ink Composition

Next, the ink compositions of the examples and the comparative examples were prepared and then evaluated. In Tables 1, 2, and 3, the compositions of the ink compositions of the examples and the comparative examples are shown. After the components (materials) of the ink composition were blended and stirred in accordance with the composition shown in each of Tables 1 to 3 so as to be uniformly mixed together, the mixture thus obtained was filtrated using a membrane filter (pore size: 1 μm), so that the ink composition was prepared. The pH of the ink composition thus prepared was measured immediately after the preparation thereof using a pH meter (desktop pH meter F-74, manufactured by Horiba, Ltd.).

In Tables 1 to 3, the unit of the value represents percent by mass. In addition, the column with no value represents that no material is contained. In addition, among the components shown in the tables, 1,5-pentanediol (1,5-PD), diethylene glycol (DEG), 2-pyrrolidone (2-P), triethylene glycol monobutyl ether (TEGmBE), and 1,2-hexanediol (1,2-HD) are represented by the abbreviations shown in the above parentheses.

TABLE 1

| | Component | Example 1 | Example 2 | Example 3 | Example 4 | Example 5 | Example 6 | Example 7 | Example 8 |
|---|---|---|---|---|---|---|---|---|---|
| Color Material (Dye) | C.I. Reactive Black 39 | 10.00 | | | | | | | |
| | C.I. Reactive Red 3:1 | 2.00 | | | | | | | |
| | C.I. Reactive Blue 49 | | 8.00 | | | | | | |
| | C.I. Reactive Red 31 | | | 6.00 | | | | | |
| | C.I. Reactive Yellow 95 | | | | 10.00 | | | | |
| | C.I. Direct Blue 87 | | | | | 8.00 | | | |
| | C.I. Reactive Orange 13 | 3.00 | | | | | 10.00 | | |
| | C.I. Acid Yellow 79 | | | | | | | 4.50 | |
| | C.I. Reactive Red 24 | | | | | | | | 10.00 |
| | C.I. Acid Black 172 | | | | | | | | |
| | C.I. Acid Orange 33 | | | | | | | | |
| | C.I. Reactive Blue 15:1 | | | | | | | | |
| | C.I. Acid Red 249 | | | | | | | | |
| Organic Solvent | 1,5-PD | | | | | | 5.00 | | 5.00 |
| | DEG | 5.60 | 6.25 | 7.83 | 5.00 | 5.00 | | 5.00 | |
| | 2-P | 5.00 | 5.00 | 7.00 | 7.00 | 5.00 | 6.00 | 7.00 | 6.00 |
| Penetrating Agent | TEGmBE | 2.00 | 3.00 | | 6.00 | 2.00 | | | |
| | 1,2-HD | 1.00 | | 3.00 | | 2.00 | 3.00 | 3.00 | 5.00 |
| Surfactant | Olfine E1010 | 0.30 | | | | 1.00 | | | |
| | Olfine PD002W | | | | 0.25 | | | | |
| | Surfynol 104PG50 | 0.25 | | 0.65 | | | 1.00 | | |
| | BYK348 | | 1.00 | | | | | | 1.00 |
| | Silface SAG503A | | | | | | | 0.50 | |
| | Newcol 1006 | | | 3.00 | | | | 3.00 | |
| | C6-EO-PO-OH | | | | | 2.00 | 2.00 | | |
| | S-144 | | | | | | | | |
| Moisture-Retaining Agent/Dyeing Auxiliary Agent | Urea | 7.00 | 8.00 | 6.00 | 10.00 | 8.00 | 8.00 | 10.00 | 6.00 |
| pH Adjustor | Triethanolamine | 0.30 | 0.30 | 0.10 | 0.30 | 0.90 | 0.60 | 0.60 | 0.30 |
| | Lithium Hydroxide | 0.04 | | | 0.02 | | | | |
| | Sodium Hydroxide | | | | | | | | |
| | Potassium Hydroxide | | 0.01 | | | 0.03 | 0.05 | | |
| | BES | | | | | | | | 0.50 |
| | Adipic Acid | | | | | | | | |
| Metal Chelating Agent | MGDA·3Na | 0.05 | | | | 0.50 | | | |
| | GLDA·4Na | | 0.30 | | | | | | |
| | ASDA·4Na | | | 0.50 | | | | | |
| | HIDA·2Na | | | | | | | | 0.03 |
| | HIDS·4Na | | | | 0.06 | | | | |
| | CMGA·4Na | | | | | | 0.05 | | |
| | EDDS·3Na | | | | | | | 0.10 | |
| | IDS·4Na | | | | | | | | |
| | EDTA·2Na | | | | | | | | |
| Corrosion Inhibitor | 1,2,3-Benzotriazole | 0.01 | 0.01 | 0.01 | 0.01 | 0.01 | 0.01 | 0.01 | 0.01 |
| Antiseptic/Fungicide Agent | Proxel XL-2 | 0.30 | 0.30 | 0.30 | 0.30 | 0.30 | 0.30 | 0.30 | 0.30 |
| Water | Super Pure Water | 63.15 | 67.83 | 65.61 | 61.06 | 65.26 | 63.99 | 65.99 | 65.86 |
| Total | | 100.00 | 100.00 | 100.00 | 100.00 | 100.00 | 100.00 | 100.00 | 100.00 |

TABLE 2

| | Component | Example 9 | Example 10 | Example 11 | Example 12 | Example 13 | Example 14 | Example 15 | Example 16 |
|---|---|---|---|---|---|---|---|---|---|
| Color Material (Dye) | C.I. Reactive Black 39 | | | | | 10.00 | 10.00 | 10.00 | 10.00 |
| | C.I. Reactive Red 3:1 | | | | | 2.00 | 2.00 | 2.00 | 2.00 |
| | C.I. Reactive Blue 49 | | | | | | | | |
| | C.I. Reactive Red 31 | | | | | | | | |
| | C.I. Reactive Yellow 95 | | | | | | | | |
| | C.I. Direct Blue 87 | | | | | | | | |
| | C.I. Reactive Orange 13 | | | | | 3.00 | 3.00 | 3.00 | 3.00 |
| | C.I. Acid Yellow 79 | | | | | | | | |
| | C.I. Reactive Red 24 | | | | | | | | |
| | C.I. Acid Black 172 | 10.00 | | | | | | | |
| | C.I. Acid Orange 33 | 1.00 | | | | | | | |
| | C.I. Reactive Blue 15:1 | | 4.50 | | | | | | |
| | C.I. Acid Red 249 | | | 3.50 | 3.50 | | | | |

TABLE 2-continued

| Component | | Example 9 | Example 10 | Example 11 | Example 12 | Example 13 | Example 14 | Example 15 | Example 16 |
|---|---|---|---|---|---|---|---|---|---|
| Organic Solvent | 1,5-PD | | | 5.00 | 5.00 | 5.00 | | | |
| | DEG | 8.00 | 8.00 | | | 5.00 | 5.60 | 5.60 | 5.60 |
| | 2-P | 5.00 | 6.00 | 8.00 | 8.00 | 5.00 | 5.00 | 5.00 | 5.00 |
| Penetrating Agent | TEGmBE | 10.00 | 8.00 | 10.00 | 10.00 | 6.00 | 9.00 | 9.00 | 9.00 |
| | 1,2-HD | | 2.00 | | | | 1.00 | 1.00 | 1.00 |
| Surfactant | Olfine E1010 | 1.00 | | 1.00 | 1.00 | | 0.30 | 0.30 | 0.30 |
| | Olfine PD002W | 0.20 | | | | | | | |
| | Surfynol 104PG50 | | | | | 0.30 | 0.25 | 0.25 | 0.25 |
| | BYK348 | | | | | | | | |
| | Silface SAG503A | | | | | | | | |
| | Newcol 1006 | | | | | | | | |
| | C6-EO-PO-OH | | | | | | | | |
| | S-144 | | | | 0.80 | | | | |
| Moisture-Retaining Agent/Dyeing Auxiliary Agent | Urea | | | | | 8.00 | 7.00 | 7.00 | 7.00 |
| pH Adjustor | Triethanolamine | 0.90 | 1.00 | 0.50 | 0.50 | | 0.30 | 0.30 | 0.30 |
| | Lithium Hydroxide | | | | | | 0.04 | 0.04 | 0.04 |
| | Sodium Hydroxide | | 0.03 | | | | | | |
| | Potassium Hydroxide | 0.01 | | | | | | | |
| | BES | | | | | 1.00 | | | |
| | Adipic Acid | | | | | 0.10 | | | |
| Metal Chelating Agent | MGDA•3Na | | 0.05 | | | 0.03 | 0.05 | 0.0008 | 1.05 |
| | GLDA•4Na | | | 0.05 | 0.05 | | | | |
| | ASDA•4Na | 0.05 | | | | | | | |
| | HIDA•2Na | | | | | | | | |
| | HIDS•4Na | | | | | | | | |
| | CMGA•4Na | | | | | | | | |
| | EDDS•3Na | | | | | | | | |
| | IDS•4Na | | | | | | | | |
| | EDTA•2Na | | | | | | | | |
| Corrosion Inhibitor | 1,2,3-Benzotriazole | 0.01 | 0.01 | 0.01 | 0.01 | 0.01 | 0.01 | 0.01 | 0.01 |
| Antiseptic/Fungicide Agent | Proxel XL-2 | 0.30 | 0.30 | 0.30 | 0.30 | 0.30 | 0.30 | 0.30 | 0.30 |
| Water | Super Pure Water | 63.53 | 69.11 | 71.64 | 70.84 | 54.26 | 56.15 | 56.20 | 55.15 |
| Total | | 100.00 | 100.00 | 100.00 | 100.00 | 100.00 | 100.00 | 100.00 | 100.00 |

TABLE 3

| Component | | Example 17 | Example 18 | Comparative Example 1 | Comparative Example 2 | Comparative Example 3 | Comparative Example 4 | Comparative Example 5 |
|---|---|---|---|---|---|---|---|---|
| Color Material (Dye) | C.I. Reactive Black 39 | | 10.00 | 10.00 | 10.00 | 10.00 | 10.00 | 10.00 |
| | C.I. Reactive Red 3:1 | | 2.00 | 2.00 | 2.00 | 2.00 | 2.00 | 2.00 |
| | C.I. Reactive Blue 49 | | | | | | | |
| | C.I. Reactive Red 31 | | | | | | | |
| | C.I. Reactive Yellow 95 | | | | | | | |
| | C.I. Direct Blue 87 | | | | | | | |
| | C.I. Reactive Orange 13 | 3.00 | 3.00 | 3.00 | 3.00 | 3.00 | 3.00 | 3.00 |
| | C.I. Acid Yellow 79 | | | | | | | |
| | C.I. Reactive Red 24 | | | | | | | |
| | C.I. Acid Black 172 | | | | | | | |
| | C.I. Acid Orange 33 | | | | | | | |
| | C.I. Reactive Blue 15:1 | | | | | | | |
| | C.I. Acid Red 249 | | | | | | | |
| Organic Solvent | 1,5-PD | | | | | | | |
| | DEG | 5.60 | 5.60 | 5.60 | 5.60 | 5.60 | 5.60 | 5.60 |
| | 2-P | 5.00 | 5.00 | 5.00 | 5.00 | 5.00 | 5.00 | 5.00 |
| Penetrating Agent | TEGmBE | 9.00 | 2.00 | 9.00 | 9.00 | 9.00 | 9.00 | 9.00 |
| | 1,2-HD | 1.00 | 1.00 | 1.00 | 1.00 | 1.00 | 1.00 | 1.00 |
| Surfactant | Olfine E1010 | 0.30 | 0.30 | 0.30 | 0.30 | 0.30 | 0.30 | 0.30 |
| | Olfine PD002W | | | | | | | |
| | Surfynol 104PG50 | 0.25 | 0.25 | 0.25 | 0.25 | 0.25 | 0.25 | 0.25 |
| | BYK348 | | | | | | | |
| | Silface SAG503A | | | | | | | |
| | Newcol 1006 | | | | | | | |
| | C6-EO-PO-OH | | | | | | | |
| | S-144 | | | | | | | |
| Moisture-Retaining Agent/Dyeing Auxiliary Agent | Urea | 7.00 | 7.00 | 7.00 | 7.00 | 7.00 | 7.00 | 7.00 |
| pH Adjustor | Triethanolamine | 0.30 | 0.30 | 0.30 | 0.30 | 1.00 | | 1.00 |
| | Lithium Hydroxide | 0.04 | 0.04 | 0.04 | 0.04 | 0.05 | | 0.06 |

TABLE 3-continued

| Component | | Example 17 | Example 18 | Comparative Example 1 | Comparative Example 2 | Comparative Example 3 | Comparative Example 4 | Comparative Example 5 |
|---|---|---|---|---|---|---|---|---|
| | Sodium Hydroxide | | | | | | | |
| | Potassium Hydroxide | | | | | | | |
| | BES | | | | | | 0.20 | |
| | Adipic Acid | | | | | | 0.30 | |
| Metal Chelating Agent | MGDA•3Na | 0.40 | 0.03 | | | | 0.05 | 1.05 |
| | GLDA•4Na | | 0.02 | | | | | |
| | ASDA•4Na | | | | | | | |
| | HIDA•2Na | | | | | | | |
| | HIDS•4Na | | | | | | | |
| | CMGA•4Na | | | | | | | |
| | EDDS•3Na | | | | | | | |
| | IDS•4Na | | | 0.05 | | 0.05 | | |
| | EDTA•2Na | | | | 0.05 | | | |
| Corrosion Inhibitor | 1,2,3-Benzotriazole | 0.01 | 0.01 | 0.01 | 0.01 | 0.01 | 0.01 | 0.01 |
| Antiseptic/Fungicide Agent | Proxel XL-2 | 0.30 | 0.30 | 0.30 | 0.30 | 0.30 | 0.30 | 0.30 |
| Water | Super Pure Water | 67.80 | 63.15 | 56.15 | 56.15 | 55.44 | 55.99 | 54.43 |
| Total | | 100.00 | 100.00 | 100.00 | 100.00 | 100.00 | 100.00 | 100.00 |

As the metal chelating agent, there were used a MGDA (methyl glycine diacetic acid) 3Na salt, a GLDA (L-glutamate diacetic acid) 4Na salt, an ASDA (L-aspartic diacetic acid) 4Na salt, an HIDA (hydroxyethylimino diacetic acid) 2Na salt, an HIDS (3-hydroxy-2,2'-iminodisuccucinic acid) 4Na salt, a CMGA (dicarboxymethyl glutamic acid) 4Na salt, and an EDDS ((S,S)-ethylenediaminedisuccinic acid) 3Na salt, each of which had a relatively preferable biodegradability, and an IDS (iminodisuccinic acid) 4Na salt and an EDTA (ethylenediaminetetraacetic acid) 2Na salt, each of which had a relatively low biodegradability.

In addition, Surfynol 104PG-50 (trade name, manufactured by Air Products and Chemicals, Inc.), and Olfine E1010 and Olfine PD-002W (trade name, manufactured by Nisshin Chemical Co., Ltd.) were each an acetylene glycol compound (surfactant). BYK-348 (trade name, manufactured by BYK) and Silface SAG503A (trade name, manufactured by Nisshin Chemical Co., Ltd.) were each a silicone compound (surfactant). Newcol 1006 (trade name, manufactured by Nippon Nyukazai Co., Ltd.) and $C_6$-EO-PO—OH (poly(oxy ethylene)-poly(oxy propylene) hexyl ether) were each a polyoxyethylene compound (surfactant). S-144 (trade name, manufactured by Asahi Glass Co., Ltd.) was a fluorine compound (surfactant). BES represents N,N-bis(2-hydroxyehtyl)-2-aminoethane sulfonic acid (pH adjuster). 1,2,3-benzotriazole was a corrosion inhibitor. Proxel XL-2 (trade name, manufactured by Lonza) was an antiseptic/fungicide agent. As the other components, commercially available reagents were used.

The ink composition of Example 1 had a composition containing C.I. Reactive Black 39, C.I. Reactive Red 3: 1, and C.I. Reactive Orange 13 as the color material (dye); MGDA.3Na (0.05 percent by mass) as the metal chelating agent; a solvent (diethylene glycol and 2-pyrrolidone) having a standard boiling point of 190° C. to less than 260° C.; a pH adjuster (triethanolamine and lithium hydroxide); a penetrating agent (triethylene glycol monobutyl ether and 1,2-hexanediol); and a surfactant (acetylene glycol compound). In the composition described above, the pH was 7.0, and the ratio of the metal chelating agent to the color material was 0.003.

The ink composition of Example 2 had a composition containing C.I. Reactive Blue 49 as the color material (dye); GLDA.4Na (0.3 percent by mass) as the metal chelating agent; a solvent (diethylene glycol and 2-pyrrolidone) having a standard boiling point of 190° C. to less than 260° C.; a pH adjuster (triethanolamine and lithium hydroxide); a penetrating agent (triethylene glycol monobutyl ether); and a surfactant (silicone compound). In the composition described above, the pH was 7.5, and the ratio of the metal chelating agent to the color material was 0.038.

The ink composition of Example 3 had a composition containing C.I. Reactive Red 31 as the color material (dye); ASDA-4Na (0.5 percent by mass) as the metal chelating agent; a solvent (diethylene glycol and 2-pyrrolidone) having a standard boiling point of 190° C. to less than 260° C.; a pH adjuster (triethanolamine); a penetrating agent (1,2-hexanediol); and a surfactant (acetylene glycol compound and poly(oxy ethylene) compound). In the composition described above, the pH was 7.8, and the ratio of the metal chelating agent to the color material (content of the metal chelating agent/content of the color material) was 0.083.

The ink composition of Example 4 had a composition containing C.I. Reactive Yellow 95 as the color material (dye); HIDS.4Na (0.06 percent by mass) as the metal chelating agent; a solvent (diethylene glycol and 2-pyrrolidone) having a standard boiling point of 190° C. to less than 260° C.; a pH adjuster (triethanolamine and lithium hydroxide); a penetrating agent (triethylene glycol monobutyl ether); and a surfactant (acetylene glycol compound). In the composition described above, the pH was 7.5, and the ratio of the metal chelating agent to the color material was 0.006.

The ink composition of Example 5 had a composition containing C.I. Direct Blue 87 as the color material (dye); MGDA.3Na (0.5 percent by mass) as the metal chelating agent; a solvent (diethylene glycol and 2-pyrrolidone) having a standard boiling point of 190° C. to less than 260° C.; a pH adjuster (triethanolamine and potassium hydroxide); a penetrating agent (triethylene glycol monobutyl ether and 1,2-hexanediol); and a surfactant (acetylene glycol compound and poly(oxy ethylene) compound). In the composition described above, the pH was 8.5, and the ratio of the metal chelating agent to the color material was 0.063.

The ink composition of Example 6 had a composition containing C.I. Reactive Orange 13 as the color material (dye); CMGA.4Na (0.05 percent by mass) as the metal chelating agent; a solvent (1,5-pentanediol and 2-pyrrolidone) having a standard boiling point of 190° C. to less than 260° C.; a pH adjuster (triethanolamine and potassium hydroxide); a penetrating agent (1,2-hexanediol), and a surfactant (acetylene glycol compound and poly(oxy ethylene) compound). In the composition described above, the pH was 8.3, and the ratio of the metal chelating agent to the color material was 0.005.

The ink composition of Example 7 had a composition containing C.I. Acid Yellow 79 as the color material (dye); EDDS.3Na (0.1 percent by mass) as the metal chelating agent; a solvent (diethylene glycol and 2-pyrrolidone) having a standard boiling point of 190° C. to less than 260° C.; a pH adjuster (triethanolamine); a penetrating agent (1,2-hexanediol), and a surfactant (silicone compound and poly (oxy ethylene) compound). In the composition described above, the pH was 8.6, and the ratio of the metal chelating agent to the color material was 0.022.

The ink composition of Example 8 had a composition containing C.I. Reactive Red 24 as the color material (dye); HIDA.2Na (0.03 percent by mass) as the metal chelating agent; a solvent (1,5-pentanediol and 2-pyrrolidone) having a standard boiling point of 190° C. to less than 260° C.; a pH adjuster (triethanolamine and BES); a penetrating agent (1,2-hexanediol); and a surfactant (silicone compound). In the composition described above, the pH was 7.3, and the ratio of the metal chelating agent to the color material was 0.003.

The ink composition of Example 9 had a composition containing C.I. Acid Black 172 and C.I. Acid Orange 33 as the color material (dye); ASDA.4Na (0.05 percent by mass) as the metal chelating agent; a solvent (diethylene glycol and 2-pyrrolidone) having a standard boiling point of 190° C. to less than 260° C.; a pH adjuster (triethanolamine and potassium hydroxide); a penetrating agent (triethylene glycol monobutyl ether); and a surfactant (acetylene glycol compound). In the composition described above, the pH was 9.0, and the ratio of the metal chelating agent to the color material was 0.005.

The ink composition of Example 10 had a composition containing C.I. Reactive Blue 15: 1 as the color material (dye); MGDA.3Na (0.05 percent by mass) as the metal chelating agent; a solvent (diethylene glycol and 2-pyrrolidone) having a standard boiling point of 190° C. to less than 260° C.; a pH adjuster (triethanolamine and sodium hydroxide); a penetrating agent (triethylene glycol monobutyl ether and 1,2-hexanediol); and a surfactant (acetylene glycol compound). In the composition described above, the pH was 9.6, and the ratio of the metal chelating agent to the color material was 0.011.

The ink composition of Example 11 had a composition containing C.I. Acid Red 249 as the color material (dye); GLDA.4Na (0.05 percent by mass) as the metal chelating agent; a solvent (1,5-pentanediol and 2-pyrrolidone) having a standard boiling point of 190° C. to less than 260° C.; a pH adjuster (triethanolamine); a penetrating agent (triethylene glycol monobutyl ether); and a surfactant (acetylene glycol compound). In the composition described above, the pH was 9.0, and the ratio of the metal chelating agent to the color material was 0.014.

The ink composition of Example 12 had the same composition as that of Example 11 except that as the compound were used. In the composition described above, the pH was 9.0, and the ratio of the metal chelating agent to the color material was 0.014.

The ink composition of Example 13 had a composition containing C.I. Reactive Black 39, C.I. Reactive Red 3: 1, and C.I. Reactive Orange 13 as the color material (dye); MGDA.3Na (0.03 percent by mass) as the metal chelating agent; a solvent (1,5-pentanediol, diethylene glycol, and 2-pyrrolidone) having a standard boiling point of 190° C. to less than 260° C.; a pH adjuster (BES and adipic acid); a penetrating agent (triethylene glycol monobutyl ether); and a surfactant (acetylene glycol compound). In the composition described above, the pH was 6.6, and the ratio of the metal chelating agent to the color material was 0.002.

The ink composition of Example 14 had a composition containing C.I. Reactive Black 39, C.I. Reactive Red 3: 1, and C.I. Reactive Orange 13 as the color material (dye); MGDA.3Na (0.05 percent by mass) as the metal chelating agent; a solvent (diethylene glycol and 2-pyrrolidone) having a standard boiling point of 190° C. to less than 260° C.; a pH adjuster (triethanolamine and lithium hydroxide); a penetrating agent (triethylene glycol monobutyl ether and 1,2-hexanediol); and a surfactant (acetylene glycol compound). In the composition described above, the pH was 7.0, and the ratio of the metal chelating agent to the color material was 0.003.

The ink composition of Example 15 had the same composition as that of Example 14 except that the content of MGDA.3Na as the metal chelating agent was set to 0.0008 percent by mass. In the composition described above, the pH was 7.0, and the ratio of the metal chelating agent to the color material was 0.0001.

The ink composition of Example 16 had the same composition as that of Example 14 except that the content of MGDA.3Na as the metal chelating agent was set to 1.05 percent by mass. In the composition described above, the pH was 7.0, and the ratio of the metal chelating agent to the color material was 0.07.

The ink composition of Example 17 had a composition containing C.I. Reactive Orange 13 as the color material (dye); MGDA.3Na (0.4 percent by mass) as the metal chelating agent; a solvent (diethylene glycol and 2-pyrrolidone) having a standard boiling point of 190° C. to less than 260° C.; a pH adjuster (triethanolamine and lithium hydroxide); a penetrating agent (triethylene glycol monobutyl ether and 1,2-hexanediol); and a surfactant (acetylene glycol compound). In the composition described above, the pH was 7.0, and the ratio of the metal chelating agent to the color material was 0.133.

The ink composition of Example 18 had the same composition as that of Example 1 except that as the metal chelating agent, MGDA.3Na (0.03 percent by mass) and GLDA.4Na (0.02 percent by mass) were used in combination. In the composition described above, the pH was 7.0, and the ratio of the metal chelating agent to the color material was 0.003.

The ink composition of Comparative Example 1 had the same composition as that of Example 1 except that as the metal chelating agent, IDS.4Na (0.05 percent by mass) was used instead of MGDA.3Na, and the amount of triethylene glycol monobutyl ether functioning as the penetrating agent was increased. In the composition described above, the pH was 7.0, and the ratio of the metal chelating agent to the color material was 0.003.

The ink composition of Comparative Example 2 had the same composition as that of Example 1 except that as the metal chelating agent, EDTA.2Na (0.05 percent by mass) was used instead of MGDA.3Na, and the amount of triethylene glycol monobutyl ether functioning as the penetrating agent was increased. In the composition described above, the pH was 7.0, and the ratio of the metal chelating agent to the color material was 0.003.

The ink composition of Comparative Example 3 had the same composition as that of Example 1 except that as the metal chelating agent, IDS.4Na (0.05 percent by mass) was used instead of MGDA.3Na, the amounts of triethanolamine and lithium hydroxide, each of which functioned as the pH adjuster, were increased, and the amount of triethylene glycol monobutyl ether functioning as the penetrating agent was increased. In the composition described above, the pH was 9.5, and the ratio of the metal chelating agent to the color material was 0.003.

The ink composition of Comparative Example 4 had the same composition as that of Example 1 except that as the ph adjuster, BES and adipic acid were used instead of triethanolamine and lithium hydroxide, and the amount of triethylene glycol monobutyl ether functioning as the penetrating agent was increased. In the composition described above, the pH was 5.8, and the ratio of the metal chelating agent to the color material was 0.003.

The ink composition of Comparative Example 5 had the same composition as that of Example 1 except that as the metal chelating agent, MGDA.3Na (1.05 percent by mass) was used, the amounts of triethanolamine and lithium hydroxide, each of which functioned as the pH adjuster, were increased, and the amount of triethylene glycol monobutyl ether functioning as the penetrating agent was increased. In the composition described above, the pH was 10.5, and the ratio of the metal chelating agent to the color material was 0.07.

Storage Stability
Change in Physical Properties

As for the ink compositions of the examples and the comparative examples, the pH stability was investigated as the index of the change in physical properties relating to the storage stability. The ink composition was filled in a glass-made sample bottle and was left alone at 60° C. for 7 days. The pH of the ink composition left alone as described above was measured and compared to the pH measured immediately after the preparation thereof, and the amount of change in pH was calculated. The amount of change in pH was evaluated in accordance with the following criteria, and the results are shown in Tables 4 and 5.

A: The amount of changed in pH is less than 1.
B: The amount of changed in pH is 1 to less than 2.
C: The amount of changed in pH is 2 to less than 3.
D: The amount of changed in pH is 3 or more.

Generation of Foreign Materials

Next, as the index of the generation of foreign materials relating to the storage stability, a high temperature storage evaluation was performed. First, approximately 30 mL of the ink composition of each of the examples and the comparative examples was filled in an evaluation ink pack in a sealed state so that no air layer was present therein and was then left alone at 60° C. for 5 days. Subsequently, 10 mL of the ink composition was filtrated using a metal mesh filter (pore size: 10 μm), and the number of crystalline foreign materials trapped by the metal mesh filter per 1 $mm^2$ was counted. Based on the number thus obtained, the generation of foreign materials of the ink composition was evaluated in accordance with the following criteria. The results are shown in Tables 4 and 5.

A: The number of foreign materials per 1 $mm^2$ is less than 5.
B: The number of foreign materials per 1 $mm^2$ is 5 to less than 10.
C: The number of foreign materials per 1 $mm^2$ is 10 to less than 30.
D: The number of foreign materials per 1 $mm^2$ is 30 or more.

Change in Chromogenic Property (Change in Color Optical Density)

First, a pre-treatment liquid to be used in a pre-treatment step was prepared. In particular, after 5 parts by mass of a poly(oxy ethylene) diisopropyl ether (oxy ethylene: 30 moles), 5 parts by mass of sodium alginate, 100 parts by mass of urea (hydrotropic agent), and 10 parts by mass of sodium m-benzene sulfonate were well mixed together, while the mixture thus prepared was gradually added to 1,000 parts by mass of ion exchanged water, stirring was performed at 60° C. for 30 minutes. Next, 30 parts by mass of sodium carbonate (alkali agent) was further added to the solution which was being stirred and was stirred for 10 minutes. This solution was filtrated using a membrane filter having a pore diameter of 10 μm, so that the pre-treatment liquid was obtained.

After the pre-treatment liquid was applied to a cloth (silk, plain-woven) using a sprayer and was then squeezed to a pickup rate of 20% by a mangle, the cloth was dried. Subsequently, an ink composition α which was the ink composition left alone at room temperature for 5 days after the manufacturing thereof and an ink composition β which was the ink composition left alone at 60° C. for 5 days were filled in respective ink cartridges of an ink jet printer PX-G930 (manufactured by Seiko Epson Corp.) and were adhered to the respective cloths thus pre-treated, so that an image was textile-printed. The image resolution was set to 1,440×720 dpi (Dots Per Inch). After a steaming treatment was performed at 102° C. for 10 minutes on the cloth on which the image was textile-printed, washing was performed at 60° C. for 10 minutes using an aqueous solution containing 0.2 percent by mass of Laccol STA (surfactant, manufactured by Meisei Chemical Works, Ltd.), and drying was then performed, so that an evaluation sample was obtained. In this case, in particular, the "room temperature" indicates a range of 15° C. to 25° C.

The evaluation of the chromogenic property was performed by measuring an OD value (coloring density) using a colorimeter (trade name: "Gretag Macbeth Spectrolino", manufactured by X-Rite), and by the use of the OD value thus measured, the chromogenic property of the image of each of the ink composition α and the ink composition β was evaluated based on the following calculation equation and evaluation criteria. The results are shown in Tables 4 and 5.

Change in chromogenic property=OD value obtained from textile printing of the ink composition β (left alone at 60° C. for 5 days)/OD value obtained from textile printing of the ink composition α (left alone at room temperature after the manufacturing)

A: The change in chromogenic property is 0.9 or more.
B: The change in chromogenic property is 0.7 to less than 0.9.
C: The change in chromogenic property is 0.5 to less than 0.7.
D: The change in chromogenic property is less than 0.5.

Biodegradability

The biodegradability was evaluated with reference to the chemical material standard which satisfies the GOTS (Global Organic Textile Standard) certificate. In particular, the biodegradability was evaluated by whether the ink composition does not include substance group which are listed in GOTS Version 5.0, 2,3,1 Prohibited and restricted inputs, Complexing agents and surfactants. And the results are shown in Tables 4 and 5.

A: The GOTS certificate is satisfied.
D: The GOTS certificate is not satisfied.

Clogging Recovery Property

The clogging recovery property of a nozzle of an ink jet head was evaluated using the ink composition of each of the examples and the comparative examples. In particular, the ink composition was filled in an ink cartridge of an ink jet printer PX-G930 (manufactured by Seiko Epson Corp.), and the ink cartridge was set in the printer described above. Subsequently, in a 40° C.-environment, a 100%-duty solid pattern was continuously printed on regular paper for 5 minutes. Next, while the above printing was performed, at a timing at which the carriage of the printer is located above the regular paper, an electrical power code was pulled out of an electrical outlet. After the printer in the state described above was left alone in a 40° C.-environment for 2 days, the printer was placed in a room-temperature environment and was electrically connected by inserting the electrical power code into the electrical outlet. After head cleaning was automatically driven, a nozzle check pattern of a printer driver was printed, so that the generation of an ejection failure, such as non-ejection from the nozzle of the ink jet head, was confirmed. When the nozzle had an ejection failure (clogging), the head cleaning and the printing of the nozzle check pattern were repeatedly performed, and the number of cleanings at which no ejection failure occurred was investigated. The number of cleanings required for clogging recovery (recovery from the ejection failure) was evaluated in accordance with the following criteria. The results are shown in Table 3.

A: The number of cleanings for recovery is 3 or less.
B: The number of cleanings for recovery is 4 to 6.
C: The number of cleanings for recovery is 7 to 9.
D: The number of cleanings for recovery is 10 or more or, or the recovery cannot be achieved.

Corrosion of Ink-Repellent Film

A nozzle plate covered with an ink-repellent film formed by co-precipitation plating was prepared. In particular, a SUS316-made nozzle plate was immersed in a plating liquid (240 g/L of nickel sulfate, 45 g/L of nickel chloride, 35 g/L of boric acid, and 50 g/L of PTFE), and co-precipitation plating was performed on the nozzle plate at a pH of 4.0 to 4.5, a plating temperature of 60° C., and a cathode current density of 3 A/dm$^2$ while the plating liquid was slowly stirred.

Next, after 20 g of the ink composition of each of the examples and the comparative examples was weighed in a Teflon (registered trade name)-made container, the nozzle plate processed by the co-precipitation was immersed therein, and the container was sealed with a lid. In the state as described above, the ink composition in the container was left alone at 60° C. for 3 days, and the condition of the ink-repellent film on the surface of the nozzle plate was then observed by visual inspection. In addition, a time for repelling the ink composition (ink-repellent time) at the initial stage was compared to that after the ink composition was left alone as described above. Ink-repellent time means the time from the state where the ink adheres to the entire surface of the nozzle plate until the ink repels and forms an ink droplet on nozzle plate. Ink-repellent time is evaluated by measuring the time which the ink composition is repelled on the nozzle plate that was picked up from the ink composition. In particular, ink-repellent time is evaluated by measuring the time which the ink composition forms an ink droplet on nozzle plate. The results thus obtained were evaluated as the index of the corrosive property of the ink composition in accordance with the following criteria and are shown in Tables 4 and 5. In addition, when the ink-repellent film is degraded, and the ink-repellent property was degraded, the ink composition was not likely to be repelled, and hence, the ink-repellent time was increased.

A: The appearance of the ink-repellent film is equivalent to that at the initial state (before left alone) and is not changed therefrom, and the ink-repellent time is not increased.

B: Although the appearance of the ink-repellent film is not changed, the ink-repellent time is increased.

C: The appearance of the ink-repellent film is changed, and the ink-repellent time is increased.

D: The ink-repellent film is peeled off so that the underlayer is exposed, and the ink-repellent function is not observed.

TABLE 4

| Evaluation Result | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| Change in Physical Properties (Storage Stability) | A | A | A | A | A | A | A | A | A | A | A | A |
| Generation of Foreign Materials (Storage Stability) | A | A | A | A | A | A | A | A | A | A | A | A |
| Change in Chromogenic Property (Storage Stability) | A | A | A | A | A | A | A | A | A | A | A | A |
| Biodegradability | A | A | A | A | A | A | A | A | A | A | A | A |
| Clogging Recovery Property | A | A | A | A | A | A | A | A | A | A | A | A |
| Corrosion of Ink-Repellent Film | A | A | A | A | A | A | A | A | A | A | A | A |

TABLE 5

| Evaluation Result | Example 13 | Example 14 | Example 15 | Example 16 | Example 17 | Example 18 | Comparative Example 1 | Comparative Example 2 | Comparative Example 3 | Comparative Example 4 | Comparative Example 5 |
|---|---|---|---|---|---|---|---|---|---|---|---|
| Change in Physical Properties (Storage Stability) | A | A | A | B | A | A | A | A | A | A | B |
| Generation of Foreign Materials (Storage Stability) | A | A | B | A | A | A | D | A | C | C | A |
| Change in Chromogenic Property (Storage Stability) | A | A | A | A | A | A | A | A | D | A | D |
| Biodegradability | A | A | A | A | A | A | A | D | A | A | A |
| Clogging Recovery Property | B | A | B | A | B | A | D | A | B | B | C |
| Corrosion of Ink-Repellent Film | A | A | A | A | A | A | A | A | A | D | A |

As shown in Tables 4 and 5, in Examples 13, 15, 16, and 17, except that one or two evaluation items were evaluated as B corresponding to a "good" level, the other evaluation items were all evaluated as A corresponding to an "excellent" level. In the other examples, all the evaluation items were evaluated as A. Accordingly, it was found that the ink compositions of Examples 1 to 18 were excellent in storage stability (change in physical properties, generation of foreign materials, and change in chromogenic property), biodegradability, and clogging recovery property and could reduce the corrosion of the ink-repellent film. In addition, as for the chromogenic property, it was also found that since the pre-treatment liquid containing sodium alginate was used, the chromogenic property of the ink composition of each of those examples was excellent.

On the other hand, Comparative Examples 1 to 5 were each evaluated as D in which at least one evaluation item corresponded to a "no good" level. In particular, in Comparative Example 1, since IDS.4Na having a relatively low chelating function was used as the metal chelating agent, the generation of foreign materials was observed, so that the generation of foreign materials and the clogging recovery property in association therewith were evaluated as D. In Comparative Example 2, since EDTA.2Na was used as the metal chelating agent, the biodegradability was evaluated as D. In Comparative Example 3, although the components were the same as those of Comparative Example 1, since the amount of the pH adjustor was increased, and the pH of the ink composition was increased, the generation of foreign materials was improved to C corresponding to an "acceptable" level. However, as the problem caused thereby, the chromogenic property was degraded to D. In Comparative Example 4, although the composition was the same as that of Example 1 except that the pH adjustor was changed, since the pH was less than 6, the generation of foreign materials and the clogging recovery property were degraded as compared to those of Example 1. In addition, the corrosion of the ink-repellent film was evaluated as D. In Comparative Example 5, since the amount of MGDA.3Na functioning as the metal chelating agent was more than 1 percent by mass, and the pH was more than 10 by the increase in amount of the pH adjustor, the change in chromogenic property was evaluated as D. From the results described above, it was found that Comparative Examples 1 to 5 were inferior to the examples.

The invention is not limited to the embodiments described above and may be appropriately changed and/or modified within the scope of the claims and the specification or without departing from the spirit of the claims and the specification, and the ink compositions thus changed and/or modified are also to be included in the technical scope of the invention.

The entire disclosures of Japanese Patent Application Nos. 2016-187870, filed Sep. 27, 2016 and 2017-132513, filed Jul. 6, 2017 are expressly incorporated by reference herein.

What is claimed is:

1. An ink jet textile printing ink composition comprising:
   water;
   a color material, wherein the color material has a halogenated triazine structure in its molecule; and
   a metal chelating agent,
   wherein the metal chelating agent includes at least one selected from methyl glycine diacetic acid (MGDA), L-glutamate diacetic acid (GLDA), L-aspartic diacetic acid (ASDA), hydroxyethylimino diacetic acid (HIDA), 3-hydroxy-2,2'-iminodisuccucinic acid (HIDS), dicarboxymethyl glutamic acid (CMGA), (S,S)-ethylenediaminedisuccinic acid (EDDS), and salts thereof, and
   the ink composition has a pH of 6 to 10.

2. The ink jet textile printing ink composition according to claim 1,
   wherein a content of the metal chelating agent with respect to a total mass of the ink composition is 0.005 to 1.1 percent by mass.

3. The ink jet textile printing ink composition according to claim 2,
   wherein a ratio of the metal chelating agent to the color material is 0.001:1 to 0.15:1.

4. The ink jet textile printing ink composition according to claim 1, further comprising:

at least one selected from a pH buffer, an organic amine compound, and an inorganic alkali compound.

5. The ink jet textile printing ink composition according to claim 1, further comprising:
   at least one selected from a glycol ether compound and a 1,2-alkanediol; and
   at least one selected from a silicone compound, a fluorine compound, an acetylene glycol compound, and a poly(oxy ethylene) compound.

6. The ink jet textile printing ink composition according to claim 1, further comprising:
   at least two types of solvents having a boiling point at one atmospheric pressure of 190° C. to less than 260° C. in an amount of 10 to 30 percent by mass with respect to the total mass of the ink composition,
   wherein the solvents include a nitrogen-containing heterocyclic compound and an alkylpolyol,
   a content of the nitrogen-containing heterocyclic compound is 5 to 20 percent by mass with respect to a total mass of the ink composition, and
   a content of the alkylpolyol is 5 to 20 percent by mass with respect to the total mass of the ink composition.

7. The ink jet textile printing ink composition according to claim 1,
   wherein the ink composition is configured for storage in an ink receiving container that includes a member containing a fatty acid compound.

8. An ink receiving container that includes a member containing a fatty acid compound,
   wherein the container is configured for storage of the ink jet textile printing ink composition according to claim 1.

9. An ink receiving container that includes a member containing a fatty acid compound,
   wherein the container is configured for storage of the ink jet textile printing ink composition according to claim 2.

10. An ink receiving container that includes a member containing a fatty acid compound,
    wherein the container is configured for storage of the ink jet textile printing ink composition according to claim 3.

11. An ink receiving container that includes a member containing a fatty acid compound,
    wherein the container is configured for storage of the ink jet textile printing ink composition according to claim 4.

12. An ink receiving container that includes a member containing a fatty acid compound,
    wherein the container is configured for storage of the ink jet textile printing ink composition according to claim 5.

13. An ink receiving container that includes a member containing a fatty acid compound,
    wherein the container is configured for storage of the ink jet textile printing ink composition according to claim 6.

14. An ink receiving container that includes a member containing a fatty acid compound,
    wherein the container is configured for storage of the ink jet textile printing ink composition according to claim 7.

* * * * *